(12) United States Patent
Frydman et al.

(10) Patent No.: US 11,096,654 B2
(45) Date of Patent: Aug. 24, 2021

(54) NON-INVASIVE ASSESSMENT OF ANATOMIC VESSELS

(71) Applicants: Massachusetts Institute of Technology, Cambridge, MA (US); The General Hospital Corporation, Boston, MA (US)

(72) Inventors: Galit Hocsman Frydman, Boston, MA (US); Alexander Tyler Jaffe, Cambridge, MA (US); Maulik D. Majmudar, Somerville, MA (US); Mohamad Ali Toufic Najia, Cambridge, MA (US); Robin Singh, Cambridge, MA (US); Zijun Wei, Cambridge, MA (US); Jason Yang, Charlotte, NC (US); Brian W. Anthony, Cambridge, MA (US); Athena Yeh Huang, Palo Alto, CA (US); Aaron Michael Zakrzewski, Boston, MA (US)

(73) Assignees: Massachusetts Institute of Technology, Cambridge, MA (US); The General Hospital Corporation, Boston, MA (US)

( * ) Notice: Subject to any disclaimer, the term of this patent is extended or adjusted under 35 U.S.C. 154(b) by 616 days.

(21) Appl. No.: 15/952,999

(22) Filed: Apr. 13, 2018

(65) Prior Publication Data
US 2018/0296180 A1    Oct. 18, 2018

Related U.S. Application Data

(60) Provisional application No. 62/485,698, filed on Apr. 14, 2017.

(51) Int. Cl.
*A61B 8/04* (2006.01)
*A61B 8/00* (2006.01)
(Continued)

(52) U.S. Cl.
CPC ............... *A61B 8/04* (2013.01); *A61B 5/022* (2013.01); *A61B 8/0891* (2013.01);
(Continued)

(58) Field of Classification Search
CPC .................................................. A61B 5/02133
See application file for complete search history.

(56) References Cited

U.S. PATENT DOCUMENTS

| 4,446,395 A | 5/1984 | Hadjicostis |
| 5,139,020 A | 8/1992 | Koestner et al. |

(Continued)

FOREIGN PATENT DOCUMENTS

| EP | 0503839 | 8/1998 |
| EP | 2196141 | 5/2011 |

(Continued)

OTHER PUBLICATIONS

ISA, "PCT Application No. PCT/US18/27543 International Search Report and Written Opinion dated Jul. 18, 2018", 12 pages.

(Continued)

*Primary Examiner* — Yi-Shan Yang
(74) *Attorney, Agent, or Firm* — Strategic Patents, P.C.

(57) ABSTRACT

Devices, systems, and methods of the present disclosure are directed to accurate and non-invasive assessments of anatomic vessels (e.g., the internal jugular vein (IJV)) of vertebrates. For example, a piezoelectric crystal may generate a signal and receive a pulse echo of the signal along an axis extending through the piezoelectric crystal and an anatomic vessel. A force sensor disposed relative to the piezoelectric crystal may measure a force exerted (e.g., along skin of the vertebrate) on the anatomic vessel along the axis. The pulse echo received by the piezoelectric crystal and the force measured by the force sensor may, in combination, non-invasively and accurately determine a force (Continued)

response of the anatomic vessel. In turn, the force response may be probative of any one or more of a variety of different characteristics of the anatomic vessel including, for example, location of the anatomic vessel and pressure of the anatomic vessel.

17 Claims, 15 Drawing Sheets

(51) Int. Cl.
    *A61B 8/08*     (2006.01)
    *G01L 17/00*     (2006.01)
    *G01L 1/16*     (2006.01)
    *A61B 5/022*     (2006.01)
    *A61B 90/00*     (2016.01)
    *A61B 5/021*     (2006.01)
    *A61B 5/00*     (2006.01)
    *A61B 5/02*     (2006.01)

(52) U.S. Cl.
    CPC .......... *A61B 8/4427* (2013.01); *A61B 8/5223* (2013.01); *A61B 8/54* (2013.01); *A61B 8/56* (2013.01); *A61B 8/58* (2013.01); *G01L 1/162* (2013.01); *G01L 17/00* (2013.01); *A61B 5/0053* (2013.01); *A61B 5/02007* (2013.01); *A61B 5/02133* (2013.01); *A61B 2090/064* (2016.02)

(56) References Cited

U.S. PATENT DOCUMENTS

| | | | |
|---|---|---|---|
| 5,188,106 | A | 2/1993 | Nappholz et al. |
| 6,281,801 | B1 | 8/2001 | Cherry et al. |
| 6,358,208 | B1 | 3/2002 | Mendlein et al. |
| 6,702,743 | B2 | 3/2004 | Michaeli et al. |
| 6,755,789 | B2 | 6/2004 | Stringer et al. |
| 7,033,321 | B1 | 4/2006 | Sarvazyan et al. |
| 7,118,534 | B2 | 10/2006 | Ward et al. |
| 7,691,067 | B2 | 4/2010 | Popovic et al. |
| 7,815,574 | B2 | 10/2010 | Patterson et al. |
| 7,819,810 | B2 | 10/2010 | Stringer et al. |
| 7,976,471 | B2 | 7/2011 | Martin et al. |
| 8,109,880 | B1 | 2/2012 | Pranevicius et al. |
| 8,167,804 | B2 | 5/2012 | Kim et al. |
| 8,409,103 | B2 | 4/2013 | Grunwald et al. |
| 8,417,306 | B2 | 4/2013 | Cheng |
| 8,613,705 | B2 | 12/2013 | Scheurer et al. |
| 8,864,670 | B2 | 10/2014 | Lisiecki et al. |
| 8,945,016 | B2 | 2/2015 | Goharlaee et al. |
| 9,066,660 | B2 | 6/2015 | Watson et al. |
| 2004/0236223 | A1 | 11/2004 | Barnes et al. |
| 2006/0206032 | A1* | 9/2006 | Miele ........................ A61B 8/06 600/504 |
| 2007/0213616 | A1* | 9/2007 | Anderson .............. A61B 8/445 600/448 |
| 2007/0239041 | A1 | 10/2007 | Chatterjee et al. |
| 2007/0270720 | A1 | 11/2007 | Fry et al. |
| 2010/0094141 | A1 | 4/2010 | Puswella et al. |
| 2011/0004099 | A1 | 1/2011 | Kim et al. |
| 2011/0218436 | A1* | 9/2011 | Dewey ..................... A61B 8/14 600/443 |
| 2012/0172710 | A1 | 7/2012 | Anthony et al. |
| 2013/0158418 | A1 | 6/2013 | Mizukami et al. |
| 2014/0114193 | A1* | 4/2014 | Anthony ................ A61B 8/429 600/459 |
| 2014/0228683 | A1 | 8/2014 | Aoki et al. |
| 2015/0190111 | A1 | 7/2015 | Fry |
| 2016/0095572 | A1 | 4/2016 | Aguren |
| 2016/0157826 | A1* | 6/2016 | Sisodia ................. B06B 1/0215 600/454 |
| 2016/0374644 | A1* | 12/2016 | Mauldin, Jr. ......... A61B 8/5223 600/424 |
| 2017/0042431 | A1* | 2/2017 | Maltz .................... A61B 5/1075 |
| 2020/0261059 | A1* | 8/2020 | Xu ........................ A61B 8/4477 |

FOREIGN PATENT DOCUMENTS

| | | |
|---|---|---|
| WO | WO-2011066982 | 6/2011 |
| WO | WO-2012099539 | 7/2012 |
| WO | WO-2013090850 | 6/2013 |
| WO | WO-2014125431 | 8/2014 |
| WO | WO-2015103472 | 7/2015 |
| WO | WO-2015160976 | 10/2015 |
| WO | WO-2018191650 | 10/2018 |

OTHER PUBLICATIONS

ISA,"PCT Application No. PCT/US18/27543 International Preliminary Report on Patentability dated Oct. 24, 2019", 8 pages.
Zhou, Qifa et al., "Piezoelectric single crystals for ultrasonic transducers in biomedical applications", Progress in Materials Science 66, DOI: 10.1016/j.pmatsci.2014.06.001 Oct. 2014 , 51 pages.
Marcelino, Paulo et al., "Non-Invasive Evaluation of Central Venous Pressure by Echocardiography", Portuguese journal of cardiology: an official journal of the Portuguese Society of Cardiology Mar. 2002, pp. 125-133.
Lipton, Bruce, "Estimation of central venous pressure by ultrasound of the internal jugular vein", American Journal of Emergency Medicine, vol. 18, No. 4 Jul. 2000 , pp. 432-434.
Ogum, Cyprian et al., "Non-invasive central venous pressure estimation by ultrasoundguided internal jugular vein cross-sectional area measurement", Biomedical Physics & Engineering Express 2 025004 Feb. 26, 2016, 7 pages.
Sorvoja, Hannu, "Noninvasive Blood Pressure Pulse Detection and Blood Pressure Determination", University of Oulu, Faculty of Technology, Department of Electrical and Information Engineering Nov. 28, 2006, 90 pages.
Baumann, Ulrich A. et al., "Estimation of central venous pressure by ultrasound", Elsevier, Resuscitation 64 2005, pp. 193-199.
Zakrzewski, Aaron M. et al., "Non-Invasive Blood Pressure Estimation Using Ultrasound and Simple Finite Element Models", IEEE Transactions on Biomedical Engineering Jun. 12, 2017 , 12 pages.

* cited by examiner

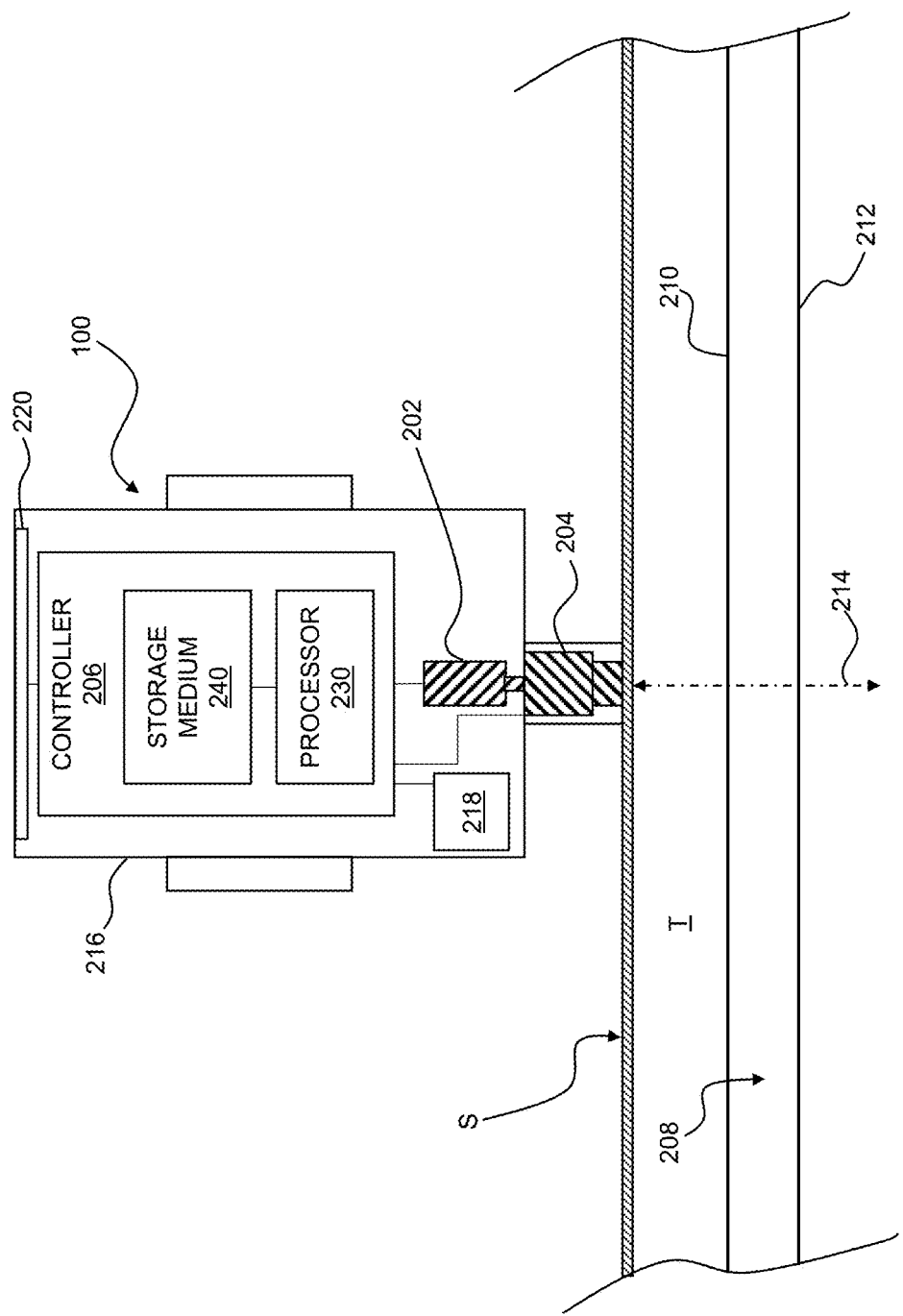

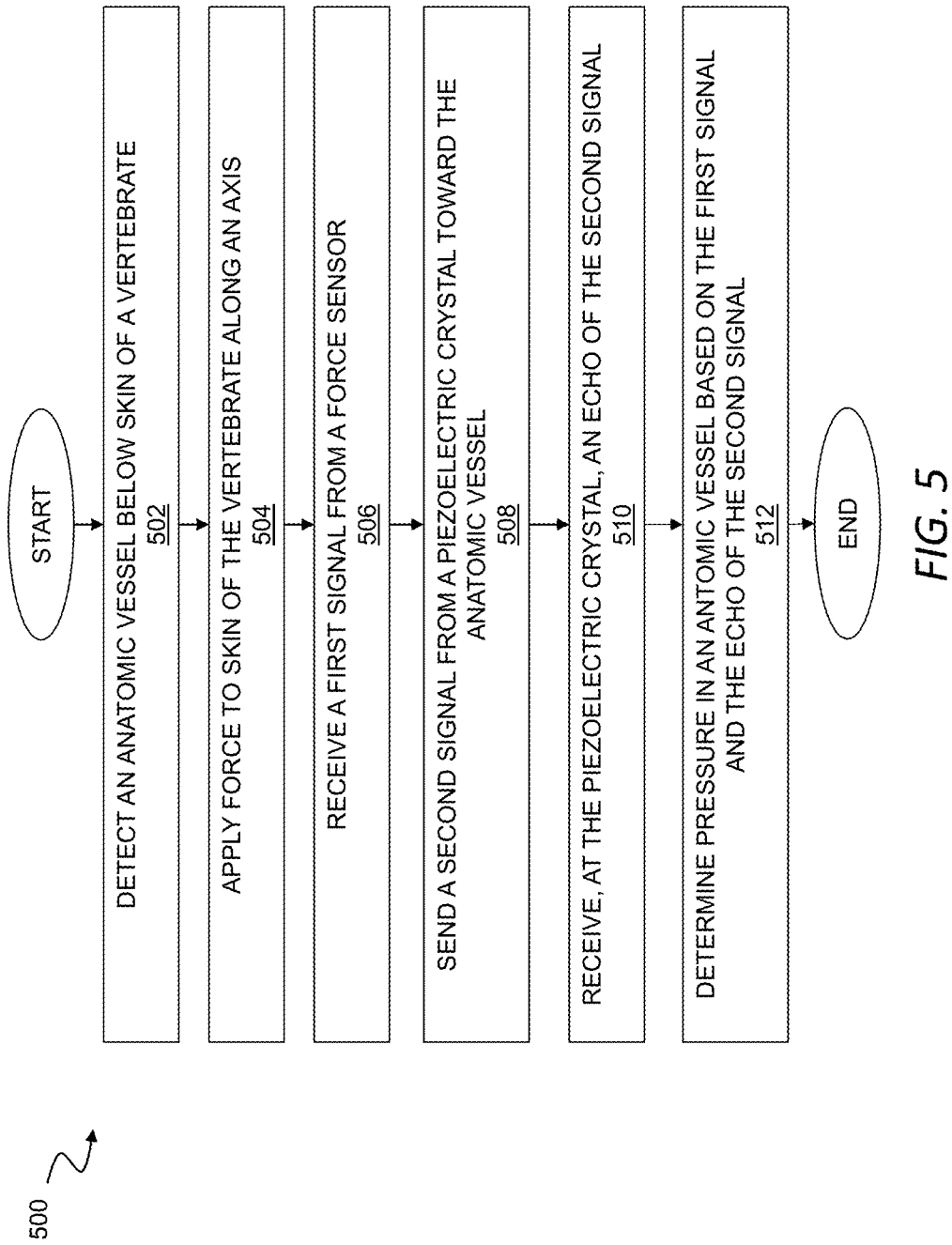

NON-INVASIVE ASSESSMENT OF ANATOMIC VESSELS

CROSS-REFERENCE TO RELATED APPLICATIONS

This application claims the benefit of U.S. Provisional Application No. 62/485,698, filed Apr. 14, 2017, the entire contents of which are incorporated herein by reference.

GOVERNMENT LICENSE RIGHTS

This invention was made with Government support under Grant No. U01-EB018813 awarded by the National Institutes of Health. The Government has certain rights in the invention.

BACKGROUND

Information regarding anatomic vessels of vertebrates can be useful for diagnosis and treatment of vertebrates. However, invasive procedures to access anatomic vessels to obtain measurements can be difficult and time-consuming. Further, the invasive procedure can itself create certain risks for the vertebrate, such as the risk of infection. Conversely, non-invasive techniques for determining information regarding anatomic vessels, while associated with fewer risks than invasive techniques, can be inaccurate to the point of having limited usefulness to physicians.

As an example, intravascular volume (IVV) status is the volume of blood in a vertebrate's circulatory system. IVV status can be a clinically significant indicator of vascular and tissue health, and imbalances in IVV status can be probative of a number of different root causes, such as fluid loss, fluid retention, fluid extravasation, or iatrogenesis. Central venous pressure (CVP) is the most clinically accepted measure of IVV status, with central venous catheter placement or right heart catheterization being the most commonly used methods of acquiring CVP. The invasiveness of these procedures and the risk of infection, however, make the use of CVP as a measure of IVV impractical or unsuitable for certain hospital and outpatient settings. Thus, clinicians sometimes rely on visual inspection of the internal and/or external jugular vein to estimate central venous pressure. However, visual assessment of the jugular veins can be subjective, user-dependent, semi-quantitative, and often inaccurate.

SUMMARY

Devices, systems, and methods of the present disclosure are directed to accurate and non-invasive assessments of anatomic vessels (e.g., the internal jugular vein (IJV)) of vertebrates. For example, a piezoelectric crystal may generate a signal and receive an echo of the signal along an axis extending through the piezoelectric crystal and an anatomic vessel. A force sensor disposed relative to the piezoelectric crystal may measure a force exerted (e.g., along skin of the vertebrate) on the anatomic vessel along the axis. The echo received by the piezoelectric crystal and the force measured by the force sensor may, in combination, non-invasively and accurately determine a force response of the anatomic vessel. In turn, the force response may be probative of any one or more of a variety of different characteristics of the anatomic vessel including, for example, location of the anatomic vessel and pressure of the anatomic vessel.

According to one aspect, a system may include a force sensor, a piezoelectric crystal and a controller. The force sensor (e.g., a load cell) may be disposed relative to the piezoelectric crystal to measure a force exerted along an axis extending through the piezoelectric crystal. The controller may be in electrical communication with the force sensor and the piezoelectric crystal. The controller may be configured to perform operations including receiving a first signal from the force sensor, the first signal indicative of the force exerted along the axis extending through the piezoelectric crystal and transmitted to the anatomic vessel below skin of the vertebrate, sending a second signal (e.g., an ultrasound signal) from the piezoelectric crystal toward the anatomic vessel in a direction substantially parallel to the axis, receiving, from the piezoelectric crystal, an echo of the second signal substantially along the axis, and, based on the first signal and one or more peaks in the echo of the second signal, determining pressure in the anatomic vessel. The system may further, or instead, include a housing. One or more of the force sensor, the piezoelectric crystal, and the controller may be at least partially disposed in the housing. The housing may, for example, be sized for single-handed manipulation by a user. Further, or instead, the system may include a battery at least partially disposed in the housing. The battery may be in electrical communication with the force sensor, the controller, and the piezoelectric crystal. Still further or instead, a user interface may be carried on the housing. The user interface may be in electrical communication with the controller. The controller may be further configured to send an indication of the pressure in the anatomic vessel to the user interface. In additional, or in the alternative, the controller may be configured to determine pressure in the anatomic vessel based on a predetermined contact area of the force sensor (e.g., the axis may extend through the contact area of the force sensor).

According to another aspect, a computer program product on a non-transitory computer readable storage medium having a plurality of instructions stored thereon which, when executed by one or more processors, may cause the one or more processors to perform operations including receiving a first signal from a force sensor, the first signal indicative of a force applied to skin of a vertebrate and transmitted along an axis extending through a piezoelectric crystal to an anatomic vessel below the skin, sending a second signal from the piezoelectric crystal toward the anatomic vessel in a direction substantially parallel to the axis, receiving, from the piezoelectric crystal, an echo of the second signal substantially along the axis, and, based on the first signal and one or more peaks in the echo of the second signal, determining pressure in the anatomic vessel.

Implementations may include one or more of the following features.

In some implementations, the force sensor and the piezoelectric crystal may be axially aligned with one another along the axis.

In certain implementations, determining pressure in the anatomic vessel may include detecting presence of the anatomic vessel, below skin of the vertebrate, based on the one or more peaks in the echo of the second signal. Determining the pressure in the anatomic vessel may further include, based on the detected presence of the anatomic vessel, sending an indication of the presence of the anatomic vessel below the skin.

In some implementations, determining the pressure in the anatomic vessel may include receiving one or more calibration parameters and to calibrate the first signal based on the one or more calibration parameters. By way of example, the one or more calibration parameters may include one or more of a body mass index of the vertebrate, a gender of the vertebrate, a height of the vertebrate, a weight of the vertebrate, and body surface area of the vertebrate. Further, or instead, the one or more calibration parameters may include a depth of the anatomic vessel from a skin surface of the vertebrate in an absence of force applied to the skin. Additionally, or alternatively, the one or more calibration parameters may include a width of the anatomic vessel in a direction parallel to the axis and in an absence of the force applied to the skin.

In certain implementations, determining pressure in the anatomic vessel includes detecting collapse of the anatomic vessel in response to the force. Determining the pressure in the anatomic vessel may be based, for example, on the detected collapse of the anatomic vessel. Further, or instead, detecting the collapse of the anatomic vessel includes identifying merger of previously discrete peaks in the echo of the second signal. Further, or instead, determining the pressure in the anatomic vessel may include determining a difference between the received first signal at a first time and the received first signal at a second time different from the first time, the received first signal at the first time corresponding to initial movement of discrete peaks in the echo of the second signal in response to the force applied to the skin, and the received first signal at the second time corresponding to merger of the previously discrete peaks in the echo of the second signal in response to the force applied to the skin.

In some implementations, the piezoelectric crystal may be disposed relative to the force sensor such that, as the force is transmitted through the force sensor to the anatomic vessel, the piezoelectric crystal is between the force sensor and the anatomic vessel.

In certain implementations, determining the pressure in the anatomic vessel may include determining pressure in the anatomic vessel based on the first signal and one or more peaks of the echo of the second signal over multiple applications of force to the skin of the vertebrate. For example, determining the pressure in the anatomic vessel may include averaging the determined pressures in the anatomic vessel over the multiple applications of force.

In some implementations, determining the pressure in the anatomic vessel may include canceling a nearfield of the echo of the second signal. For example, the nearfield of the echo of the second signal may be about the first 10 microseconds of the echo of the second signal in the time domain.

In certain implementations, determining the pressure in the anatomic vessel may include applying a Hilbert transform to the echo of the second signal in a time domain. Determining the pressure in the anatomic vessel may include, in some cases, detecting the one or more peaks in the echo signal based on the Hilbert-transformed signal. Further, or instead, tissue health (e.g., as determined by the controller) of one or more walls of the anatomic vessel may be determined based on an area under one or more peaks of the echo.

In some implementations, determining the pressure of the anatomic vessel may include determining a width of the anatomic vessel in a direction parallel to the axis and in an absence of the force applied to the skin. Determining the pressure of the anatomic vessel may include, for example, determining the width of the vessel at each of a plurality of angles of the axis relative to a surface of the anatomic vessel. Continuing with this example, determining the pressure of the anatomic vessel may include identifying a preferred direction for application of the force based on the widths of the anatomic vessel at the plurality of angles. The preferred direction for application of the force may be substantially parallel to a direction defined by an angle of the axis corresponding to a minimum width of the anatomic vessel.

According to another aspect, a computer program product on a non-transitory computer readable storage medium having a plurality of instructions stored thereon which, when executed by one or more processors, may cause the one or more processors to perform operations including receiving a first signal from a force sensor, the first signal indicative of a force applied to skin of a vertebrate and transmitted along an axis extending through an anatomic vessel below the skin, sending a second signal from a first piezoelectric crystal toward the anatomic vessel in a direction substantially parallel to the axis, receiving an echo of the second signal at a second piezoelectric crystal different from the first piezoelectric crystal, and, based on the first signal and one or more peaks in the echo of the second signal, determining pressure in the anatomic vessel.

According to yet another aspect, a method of noninvasive assessment of an anatomic vessel of a vertebrate may include detecting an anatomic vessel below skin of the vertebrate, applying a force to skin of the vertebrate along an axis extending through a piezoelectric crystal and the anatomic vessel below the skin, receiving a first signal from a force sensor, the first signal indicative of the force applied to skin of the vertebrate and transmitted to the anatomic vessel, sending a second signal from the piezoelectric crystal toward the anatomic vessel in a direction substantially parallel to the axis, receiving an echo of the second signal at the piezoelectric crystal, and, based on the first signal and one or more peaks in the echo of the signal, determining pressure in the anatomic vessel. The anatomic vessel may be a vein (e.g., an internal jugular vein) or an artery.

In certain implementations, applying the force to skin of the vertebrate may include placing the piezoelectric crystal along a base of a neck of the vertebrate. For example, placing the piezoelectric crystal along the base of the neck of the vertebrate may include placing the piezoelectric crystal such that the axis of application of the force passes through a triangle defined by a clavicle and two heads of a sternocleidomastoid of the vertebrate.

In some implementations, applying the force to the skin of the vertebrate may include moving the axis relative to the anatomic vessel through a plurality of angles and, at each angle, determining a respective width of the anatomic vessel based on the one or more peaks in the echo of the signal. The force may be applied, for example, in a direction substantially parallel to a smallest width of a plurality of widths corresponding to the plurality of angles.

BRIEF DESCRIPTION OF THE FIGURES

The foregoing and other objects, features and advantages of the devices, systems, and methods described herein will be apparent from the following description of particular embodiments thereof, as illustrated in the accompanying drawings. The drawings are not necessarily to scale, emphasis instead being placed upon illustrating the principles of the devices, systems, and methods described herein.

FIG. 2A is a schematic representation of a cross-section along section 2-2 in FIG. 1 at a stage of the assessment prior to application of force sufficient to deform the anatomic vessel.

FIG. 5 is a flow chart of an exemplary method of using a diagnostic system to non-invasively assess of an anatomic vessel of a vertebrate.

Like reference symbols in the various drawings indicate like elements.

DETAILED DESCRIPTION

Figure 1:
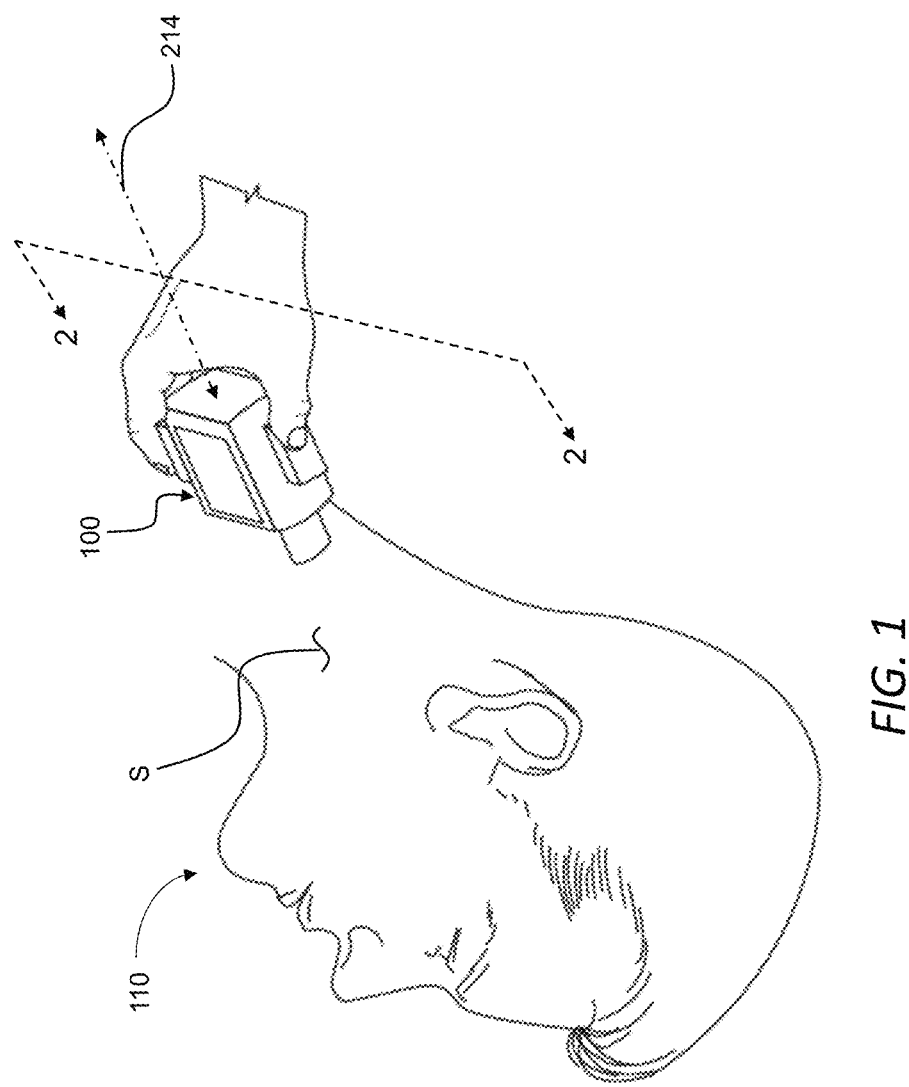
FIG. 1 is a schematic representation of a diagnostic system positioned on the neck of a vertebrate during assessment of an anatomic vessel in the neck of the vertebrate.

The embodiments will now be described more fully hereinafter with reference to the accompanying figures, in which preferred embodiments are shown. The foregoing may, however, be embodied in many different forms and should not be construed as limited to the illustrated embodiments set forth herein.

All documents mentioned herein are hereby incorporated by reference in their entirety. References to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context. Thus, the term "or" should generally be understood to mean "and/or" and, similarly, the term "and" should generally be understood to mean "and/or."

Recitation of ranges of values herein are not intended to be limiting, referring instead individually to any and all values falling within the range, unless otherwise indicated herein, and each separate value within such a range is incorporated into the specification as if it were individually recited herein. The words "about," "approximately," or the like, when accompanying a numerical value, are to be construed as indicating a deviation as would be appreciated by one of ordinary skill in the art to operate satisfactorily for an intended purpose. Ranges of values and/or numeric values are provided herein as examples only, and do not constitute a limitation on the scope of the described embodiments. The use of any and all examples, or exemplary language ("e.g.," "such as," or the like) provided herein, is intended merely to better illuminate the embodiments and does not pose a limitation on the scope of the embodiments. No language in the specification should be construed as indicating any unclaimed element as essential to the practice of the embodiments.

In the following description, it is understood that terms such as "first" "second" "above," and "below" and the like, are words of convenience and are not to be construed as limiting terms.

As used herein, unless otherwise indicated or made clear from the context, the term "physician" should be understood to include a doctor preparing for and/or performing any one or more of the medical procedures described herein and, more broadly, should be understood to include any medical personnel, such as nurses, assisting a surgeon in preparing for or performing any one or more of the medical procedures described herein. Further, as used herein, the term "vertebrate" shall be understood to include any of various different types of animals having a spinal column and, thus, includes any type of mammal, including a human, on which a medical procedure can be performed.

As also used herein, unless otherwise indicated or made clear from the context, the term "anatomic vessel" shall be understood to be any one or more anatomic structure in the body of a vertebrate and having one or more characteristics observable through the use of sonography—that is, observable by directing high-frequency acoustic pulses into the anatomic structure and observing one or more characteristics of a reflection, also referred to herein as an echo, of the high-frequency acoustic pulses. Thus, for example, an anatomic vessel may include an internal jugular vein (IJV) of a vertebrate, as may be useful in assessing jugular venous pressure (JVP) and, thus, intravenous volume (IVV) status. More generally, however, the anatomic vessel may be any of various different types of veins, arteries, organs, or combinations thereof, unless otherwise specified or made clear from the context. Further, or instead, for the sake of efficient and clear description, reference herein to walls of the anatomic vessel shall be understood to include discrete walls (as may be the case in the assessment of an organ) and/or sections of a single continuous wall (as may be the case in the assessment of a vein or artery) observable as discrete structures in a sonographic signal. As specific example, walls of an anatomic vessel may be understood to include a first section of a wall a vein or artery and a second section of the same wall of the same vein or artery, with the first section of the wall and the second section of the wall discernable from one another along an axis extending transverse to an axial direction of the vein or artery, as the case may be.

Referring now to FIGS. 1-3B, a diagnostic system 100 may include a force sensor 202, a piezoelectric crystal 204, and a controller 206. The force sensor 202 and the piezoelectric crystal 204 may each be in electrical communication with the controller 206 and, as described in greater detail below, the controller 206 may provide an accurate and non-invasive assessment an anatomic vessel 208 based on signals received from the force sensor 202 and from the piezoelectric crystal 204. As also described in greater detail below, the orientation of the force sensor 202 relative to the piezoelectric crystal 204 may offer a spatially efficient solution to the challenge of coordinating force and echo measurements into an accurate assessment of the anatomic vessel 208. For example, the force sensor 202 may be oriented relative to the piezoelectric crystal 204 to facilitate assessing the anatomic vessel 208 using only a single piezoelectric crystal or, in some cases, only a small number of piezoelectric crystals (e.g., 3 or fewer crystals). Thus, as compared to the use of an ultrasonic transducer array—used for two-dimensional or three-dimensional imaging—to assess a force response of an anatomic vessel, the diagnostic system 100 may offer advantages with respect to size, cost, complexity, or any of various other characteristics suitable for widespread use of the diagnostic system 100 across healthcare settings of varying sophistication. Further, or instead, the diagnostic system 100 may provide an absolute measurement of the pressure of the anatomic vessel 208, which may offer advantages in accuracy relative to noninvasive methods based on estimating pressure.

Figure 2B:
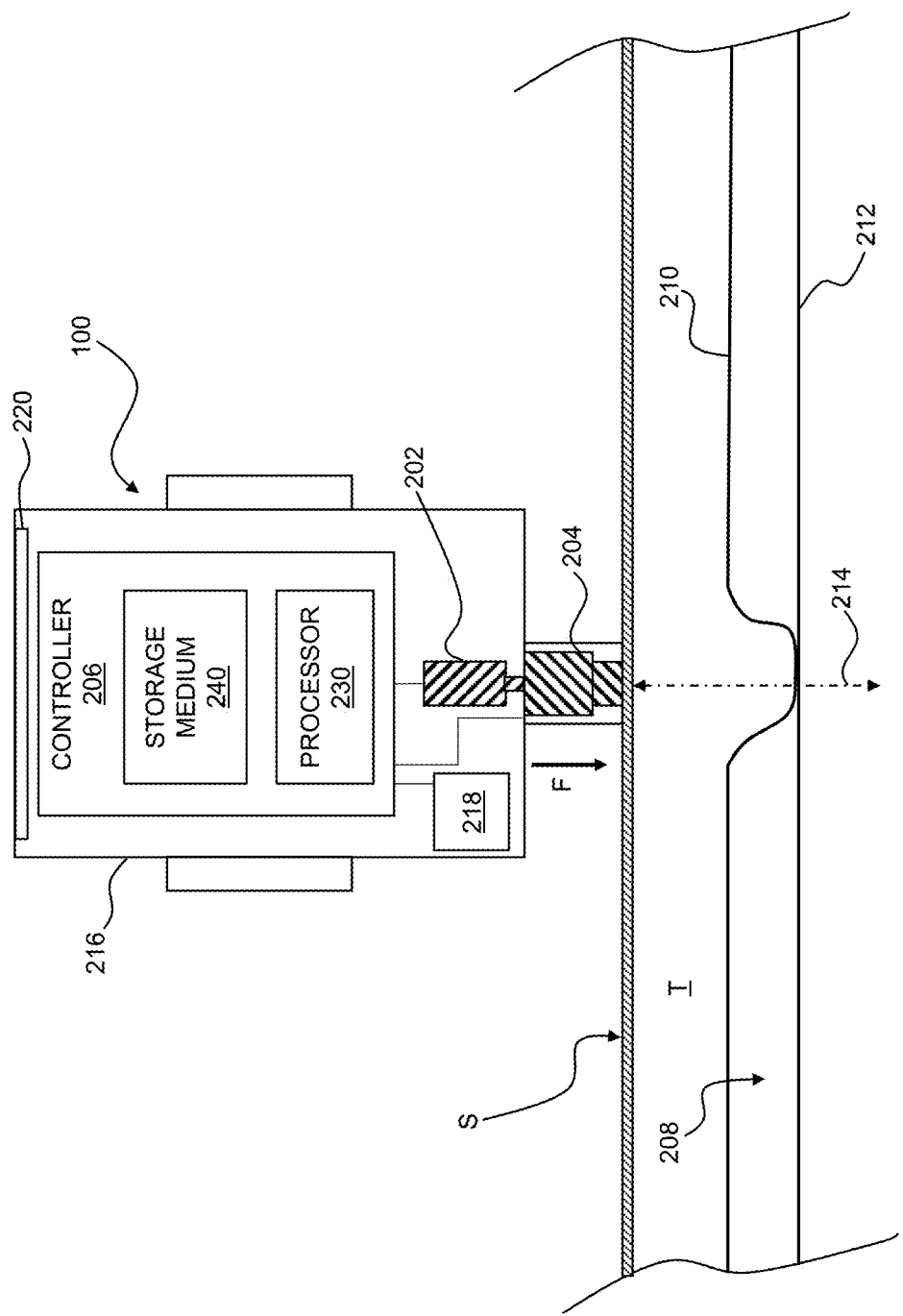
FIG. 2B is a schematic representation of the cross-section along section 2-2 in FIG. 1 at a stage of the assessment corresponding to application of force sufficient to collapse the anatomic vessel.
Figure 3A:
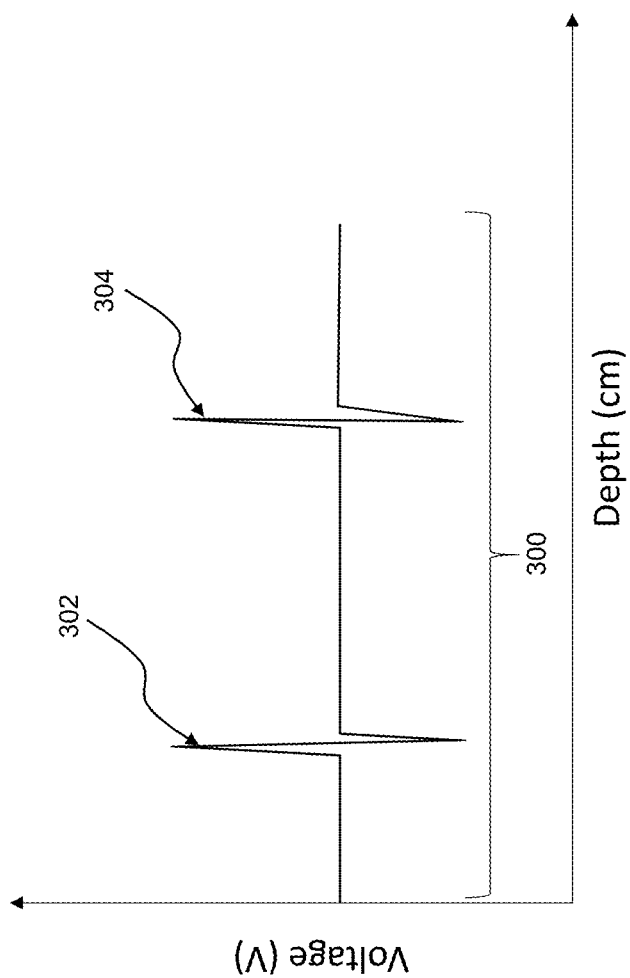
FIG. 3A is a schematic representation of an idealized echo (represented as voltage as a function of depth from a skin surface of a vertebrate and measured by a piezoelectric crystal of the diagnostic system of FIG. 1) in response to an acoustic signal directed into the anatomic vessel at the stage of the assessment, shown in FIG. 2A, prior to application of force sufficient to deform the anatomic vessel.
Figure 3B:
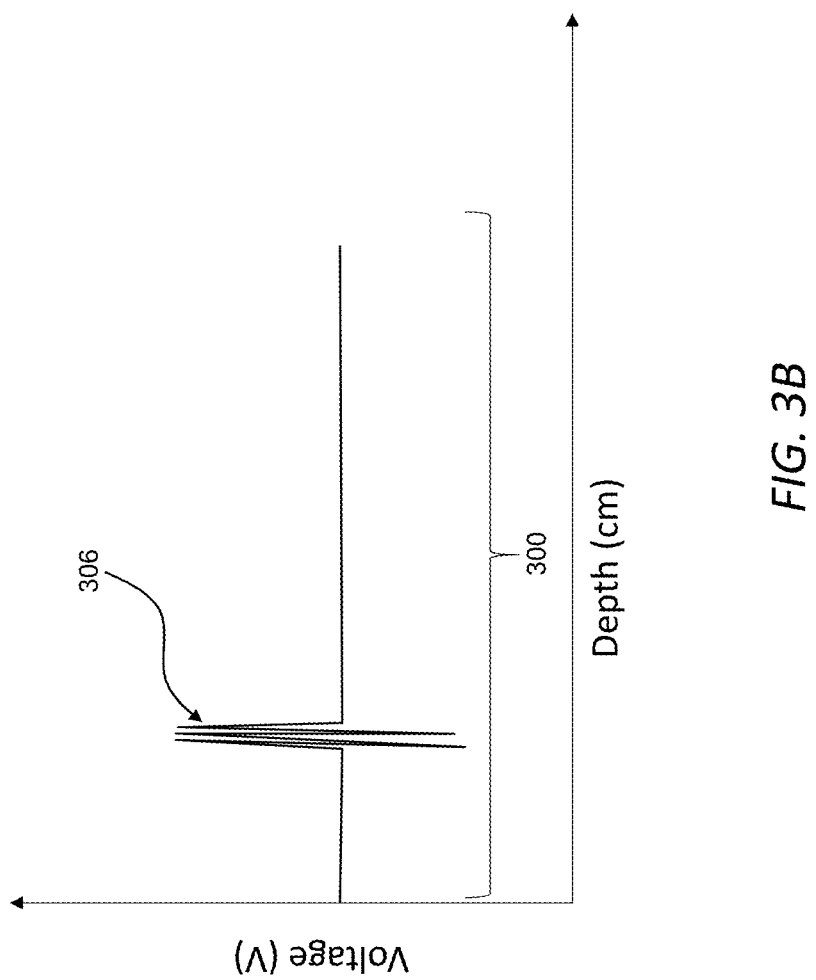
FIG. 3B is a schematic representation of an idealized echo (represented as voltage as a function of depth from a skin surface of a vertebrate and measured by a piezoelectric crystal of the diagnostic system of FIG. 1) in response to an acoustic signal directed into the anatomic vessel at the stage of the assessment, shown in FIG. 2B, corresponding to collapse of the anatomic vessel.

In use, the diagnostic system 100 may be placed on a skin surface "S" of a vertebrate 110, along a portion of the neck of the vertebrate 110, generally above an anatomic vessel 208 (e.g., the internal jugular vein) of the vertebrate 110. A physician may press the diagnostic system 100 against the skin surface "S" to apply a force "F" from the diagnostic system 100 to the skin surface "S." The direction of the force "F" applied to the skin surface "S" depends on an angle at which the physician presses the diagnostic system 100 against the skin surface "S" of the vertebrate 110. In turn, the amount of the force "F" transmitted through the tissue "T" and to the anatomic vessel 208 depends on the angle of the force "F" applied to the skin surface "S." For the sake of clarity of explanation, FIGS. 2A and 2B depict an instance in which the force "F" is aligned with the anatomic vessel 112 such that all of the force "F" is transmitted to the anatomic vessel 208 to act as a compressive force on the anatomic vessel 208 (FIGS. 2B and 3B). However, it should be appreciated that, in some instances, the force "F" may be transmitted at an angle relative to the anatomic vessel 108 such that only a component of the force "F" acts as a compressive force. As described in greater detail below, the diagnostic system 100 may be used to provide feedback useful to the physician to achieve the alignment of the force "F" relative to the anatomic vessel 108 shown in FIGS. 2A and 2B.

The force sensor 202 may measure a component of the magnitude of the force "F." Additionally, or alternatively, the piezoelectric crystal 204 may measure an echo 300 (e.g., a raw A mode pulse echo scan) formed as acoustic pulses directed from the piezoelectric crystal 204 toward the anatomic vessel 208 reflect off of the anatomic vessel 208 and return to the piezoelectric crystal 204 in a manner generally understood in sonography. Based on these force and echo signals, the controller 206 may make an assessment of the anatomic vessel 208, as also described in greater detail below. As used herein, unless otherwise specified or made clear from the context, an assessment of the anatomic vessel 208 shall be understood to include any of various different types analyses of the anatomic vessel 208 based on a change to the echo 300 in response to the measured component of the force "F." Thus, in the description that follows locating the anatomic vessel 108, positioning the diagnostic system 100 in a proper orientation relative to the anatomic vessel 108, measuring pressure of the anatomic vessel 208, and analyzing health of tissue of the anatomic vessel 108 are examples of assessments that may be made by the controller 206 based on the signals received from the force sensor 202 and the piezoelectric crystal 204.

In general, the force sensor 202 and the piezoelectric crystal 204 may be one-dimensional sensors, which—as compared to multi-dimensional counterparts—may be useful for accommodating size, cost, and complexity constraints associated with deployment of the diagnostic system 100 across many different clinical settings. For example, the piezoelectric crystal 104 may be a single crystal activatable to send an acoustic pulse (e.g., an ultrasound signal) in a direction substantially parallel to an axis 214 extending through the piezoelectric crystal 204 and the anatomic vessel 208. In response to the acoustic pulse, the piezoelectric crystal 104 may receive the echo 300 in a direction substantially parallel to the axis 214, with discrete voltage peaks 302 and 304 (FIG. 3A) in the echo 300 corresponding to depth of walls 210, 212 of the anatomic vessel 208 below the skin surface "S." That is, in such instances, the echo 300 is a one-dimensional measurement of depth of the walls 210, 212 of the anatomic vessel 208 below the skin surface "S." Additionally, or alternatively, the force sensor 202 may be a load cell or any other sensor known in the art for measuring a force (e.g., a normal force) in a single direction.

To facilitate assessment of the anatomic vessel 208 based on one-dimensional force and echo measurements, the force sensor 202 and the piezoelectric crystal 204 may be oriented relative to one another to account for the directionality of the respective measured parameters. For example, the force sensor 202 may be positioned relative to the piezoelectric crystal 204 to measure a component of the force "F" exerted along the axis 214 extending through the piezoelectric crystal 204 and transmitted to the anatomic vessel 208. In this orientation, the component of the force "F" exerted on the anatomic vessel 208 along the axis 214 may be advantageously matched to an observed change in the echo 300 measured by the piezoelectric crystal 104. This matching of applied force to corresponding changes in the echo 300 has qualitative and quantitative diagnostic value and, thus, may form the basis for any one or more of the assessments described herein.

As an example of a particularly useful indication of a force response, with the diagnostic system 100 positioned as shown in FIGS. 2A and 2B to direct the all of the force "F" into the anatomic vessel 208, the force sensor 202 may measure the force "F" applied to the anatomic vessel 208 along the axis 214 to collapse the anatomic vessel 208 from a basal state to a focally collapsed state. With respect to the echo 300, this collapse corresponds to a transition of discrete voltage peaks 302 and 304 (FIG. 3A) of the echo 300 to a single voltage peak 306 (FIG. 3B). In certain implementations, a baseline force magnitude of the force "F" applied to the anatomic vessel 208 along the axis 214 to prior to the onset of collapse of the anatomic vessel 208 may be subtracted from the measure of the force "F" to remove forces contributing to compression of tissue "T" above the anatomic vessel 208.

Continuing with the foregoing example, the force "F" required to collapse the anatomic vessel 208—with the baseline force removed, as may be useful for accounting for the presence of the tissue "T"—may be converted to pressure. The area of the diagnostic system 100 in contact with the skin surface "S" is known and intersected by the axis 214. Accordingly, the magnitude of the force "F" measured by the force sensor 202 may be converted to a pressure measurement by dividing the magnitude of the force "F" by the known contact area, and this pressure may be generally attributable to the collapse in the discrete voltage peaks 302 and 304 of the echo 300 measured along the axis 214. In this way, the diagnostic system 100 may provide a non-invasive measurement of the pressure required to collapse the anatomic vessel 208. Based on Laplace's Law, the pressure required to collapse the anatomic vessel 208 may be understood to be equal to the pressure within the anatomic vessel 208. Accordingly, the pressure measured by the diagnostic system 100 may be used by the physician as the basis for any one or more of various different clinical decisions related pressure in the anatomic vessel 208. Examples of these types of clinical decisions are described below in the context of non-invasive measurement of pressure in IJV of the vertebrate 110.

As may be appreciated from the foregoing example, the force sensor 202 and the piezoelectric crystal 204 may be advantageously positioned relative to one another to facilitate measuring force and echo (e.g., contemporaneously) without substantially without interfering with each other. For example, the force sensor 202 may be positioned outside of the path of the acoustic pulses transmitted from the piezoelectric crystal 204 and the echo measurements made by the piezoelectric crystal 204 such that the presence of the force sensor 202 has little or no impact on the operation of the piezoelectric crystal 204. As a more specific example, the piezoelectric crystal 204 may be disposed relative to the force sensor 202 such that, as the force "F" is transmitted through the force sensor 202 to the anatomic vessel 208, the piezoelectric crystal 204 is between the force sensor 202 and the anatomic vessel 208.

In general, at least a portion of the diagnostic system 100 may be sized for single-handed operation by a physician, which may be particularly useful for allowing the physician to use a free-hand to carry out one or more other aspects of diagnosis, treatment, or a combination thereof. Accordingly, by way of example and not limitation, the force sensor 202 and the piezoelectric crystal 204 may be axially aligned with one another along the axis 214. Among other advantages, such alignment may be useful for forming the diagnostic system 100 with a radial width suitable for single-handed operation of at least a portion of the diagnostic system 100.

The diagnostic system 100 may additionally, or alternatively, include a housing 216. In general, the housing 216 may be a substantially rigid structure at least partially enveloping one or more other components of the diagnostic system 100 to protect the one or more other components from an environment outside of the housing 216. For example, the housing 216 may reduce or prevent liquid ingress into the diagnostic system 100, which may be useful for deploying the diagnostic system 100 in a variety of clinical settings. Additionally, or alternatively, resistance to liquid ingress may be useful for using the diagnostic system 100 together with ultrasound gel or other similar media used to facilitate transmission of signals between the diagnostic system 100 and the anatomic vessel 208.

The housing 216 may be formed of one or more materials understood in the art to be safe for contacting the skin surface "S" of the vertebrate 110. Further, or instead, the housing 216 may be formed of one or more known materials suitable for withstanding exposure to various different bodily fluids, cleaning agents, and/or sterilization techniques (e.g., autoclaving). Thus, for example, the housing 216 may be formed of one or more different thermoplastic polymers, which may include acrylonitrile butadiene styrene (ABS) or another similar polymer.

The housing 216 may, for example, have an atraumatic shape along surfaces coming into contact with the skin surface "S" of the vertebrate 110. In this context, an atraumatic shape shall be understood to be any one or more of various different shapes that do not penetrate the skin surface "S" under the application of the force "F", in the orientation shown in FIGS. 2A and 2B, having a magnitude sufficient to collapse the anatomic vessel 208. For example, the housing 216 may have a flat surface, a curve surface, or a combination thereof useful for contacting the skin surface "S" of the vertebrate 110 with little risk of injuring the vertebrate 110 as the diagnostic system 100 is used to carry out any one or more of the measurements described herein.

In some implementations, the force sensor 202 and the piezoelectric crystal 204 may be at least partially disposed in the housing 216 such that, for example, the housing 216 may support the force sensor 202 and the piezoelectric crystal 204 in a substantially fixed orientation relative to one another. Unless otherwise specified or made clear from the context, the substantially fixed orientation of the force sensor 202 and the piezoelectric crystal 204 may correspond to any one or more of the various different relative orientations described herein with respect to the force sensor 202 and the piezoelectric crystal 204. Thus, for example, the force sensor 202 and the piezoelectric crystal may be axially aligned with one another in the housing 216. Further, or instead, the housing 216 may be sized for single-handed manipulation by the physician. Continuing with this example, the physician may grasp the housing 216 using one hand and, with any of various different one-handed grips, may move the housing 216 as necessary to carry out any one or more of the measurement techniques described herein.

Additionally, or alternatively, the controller 206 may be at least partially disposed in the housing 216. Positioning the controller 206 in the housing 216 may, for example, facilitate forming the diagnostic system 100 as a substantially self-contained unit. Such a substantially self-contained unit—particularly one that is handheld—may offer advantages in portability as compared, for example, to imaging an anatomic vessel using an ultrasound transducer array and associated hardware. Further, or instead, forming the diagnostic system 100 as a substantially self-contained unit may reduce or eliminate the need for wires and/or connectors which, in turn may be useful for reducing paths for liquid ingress into the housing 216. More generally, forming the diagnostic system 100 as a substantially self-contained unit may facilitate withstanding certain physical demands associated with handling and/or using the diagnostic system 100 in a variety of clinical settings, including settings incompatible with other types of imaging equipment (e.g., ultrasound transducer arrays).

In some implementations, the diagnostic system 100 may further include a battery 218 at least partially disposed in the housing 216. The battery 218 may be any of various different battery sources known in the art and, thus, may include one or more single-use batteries (e.g., alkaline batteries), one or more rechargeable batteries (e.g., nickel cadmium batteries, nickel metal hydride, lithium ion) or combinations thereof. The battery 218 may be a particularly useful primary or backup power source for the diagnostic system 100 in clinical settings in which power is unavailable or unreliable. In certain implementations, the battery 218 may be accessible through the housing 216 with the use of special tools, such that the battery 218 may be replaced by trained personnel. In some implementations, however, the battery 218 may be replaceable without the use of specialized tools and, thus, may be accessible within the housing 216 by removing one or more panels by hand or with the use of a Phillips head screwdriver or another ubiquitously available tool.

The diagnostic system 100 may further include a user interface 220 carried on the housing 216. As compared to a user interface away from the housing 216, the user interface 220 may reduce the need for diversion of the physician's attention to a separate screen or otherwise away from the vertebrate 110, which may be useful, for example, in an acute clinical setting. Further, or instead, as also compared to a user interface set apart from the housing 216, the user interface 220 carried on the housing 216 may facilitate forming the diagnostic system 100 as a self-contained instrument, useful in clinical settings in which portability is a significant consideration.

The user interface 220 may be any of various different types of user interfaces known in the art for receiving inputs, providing outputs, and combinations thereof. Thus, for example, the user interface 220 may include a touchscreen or other similar input/output combination useful for displaying information to the physician and for receiving inputs from the physician. In this context, the information displayed to the physician and/or the inputs received from the physician may be specific to the assessment being carried out by the diagnostic system 100 relative to the anatomic vessel 208. For example, the information displayed on the user interface 220 may be indicative of the location of the anatomic vessel 208 below the diagnostic system 100.

In certain implementations, information displayed on the user interface 220 may be information derived from the echo 300. As compared to displaying the echo 300, displaying information derived from the echo 300 may be particularly useful for implementing the user interface 220 with a display size suitable for a hand-held form factor of the diagnostic system 100. Further, or instead, as compared to displaying the echo 300, displaying information derived from the echo 300 may reduce or eliminate subjectivity that may result from forming clinical decisions based on the echo 300 itself.

In some instances, the user interface 220 may include any manner and form of audible alerts, vibration, and combinations thereof, useful, for providing non-visual alert to the physician. Thus, for example, the user interface 220 may generate a non-visual alert to indicate the location of the anatomic vessel 208 below the skin surface "S" of the vertebrate 110. Further, or instead, the non-visual alert may usefully convey to the physician ancillary information, such as a low-battery alert, related to the maintenance and operation of the diagnostic system 100.

The user interface 220 may be in electrical communication with the controller 206. Thus, for example, the physician may interact with the user interface 220 to provide to the controller 206 any of various different inputs, such as any one or more of the various different calibration parameters described herein. Further, or instead, the physician may interact with the user interface 220 to receive from the controller 206 any of various different outputs, particularly one or more outputs related to an indication of the pressure in the anatomic vessel 208 of the vertebrate 110.

In general, the controller 206 may include one or more processors 230 and a non-transitory, computer-readable storage medium 240 having stored thereon computer executable instructions for causing the one or more processors 230 to communicate with at least the force sensor 202 and the piezoelectric crystal 204 to assess the anatomic vessel 208 according to any one or more of the methods described in greater detail below.

Figure 4:
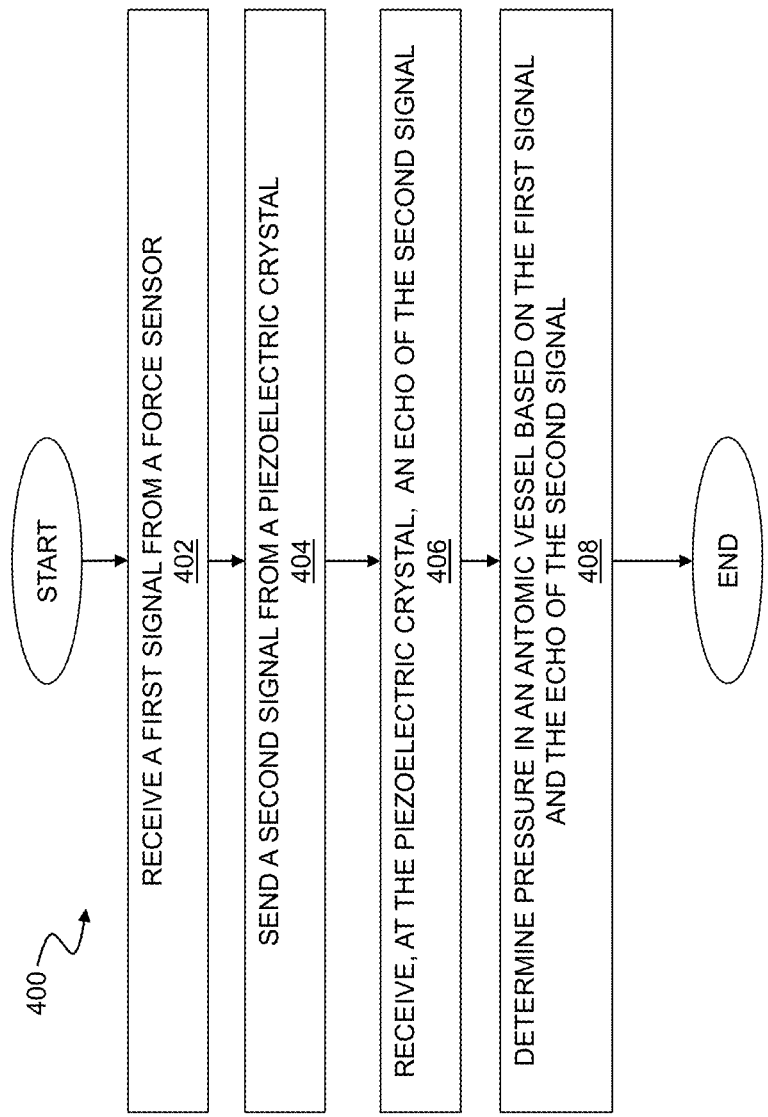
FIG. 4 is a flow chart of an exemplary method of non-invasive assessment of an anatomic vessel of a vertebrate.

FIG. 4 is a flow chart of an exemplary method 400 of non-invasive assessment of an anatomic vessel of a vertebrate. In general, unless otherwise specified or made clear from the context, the exemplary method 400 may be carried out using any one or more of the diagnostic systems described herein. Thus, for example, one or more of the steps of the exemplary method 400 may be carried out by the controller 206 (FIG. 2) of the diagnostic system 100 (FIG. 1).

As shown in step 402, the exemplary method may include receiving a first signal from a force sensor. The force sensor may be any one or more of the force sensors described herein and, thus, may include any one or more of the features of the force sensor 202 (FIG. 2). For example, the first signal may be indicative of a force applied to skin of the vertebrate with the force sensor in a known spatial relationship to a piezoelectric crystal (e.g., the piezoelectric crystal 204 in FIG. 2). The known spatial relationship may be generally useful for relating force and echo measurements to one another according to any one or more of the techniques described herein. Thus, as a more specific example, the first signal may be indicative of a force applied to skin of the vertebrate and transmitted along an axis (e.g., a center axis) extending through the piezoelectric crystal to an anatomic vessel below the skin.

As shown in step 404, the exemplary method 400 may include sending a second signal from the piezoelectric crystal toward the anatomic vessel in a direction substantially parallel to the axis. The piezoelectric crystal may be any one or more of the piezoelectric crystals described herein and, thus, may include any one or more of the features of the piezoelectric crystal 204. More specifically, sending the second signal from the piezoelectric crystal toward the anatomic vessel may include sending an acoustic pulse (e.g., an ultrasonic signal) toward the anatomic vessel in a direction substantially parallel to the axis.

As shown in step 406, the exemplary method 400 may include receiving, from the piezoelectric crystal, an echo of the second signal received by the piezoelectric crystal substantially along the axis. The echo may include one or more features of the echo 300 (FIGS. 3A and 3B). Accordingly, the echo may be a signal received by the piezoelectric crystal as the second signal sent from the piezoelectric crystal reflects off of walls of the anatomic vessel and returns back to the piezoelectric crystal. In a proper orientation relative to the anatomic vessel and in the absence of the force applied to skin of the vertebrate, the echo may include two discrete peaks representing respective depths of walls of the anatomic vessel along the axis.

As shown in step 408, the exemplary method 400 may include determining pressure in the anatomic vessel based on the first signal and one or more peaks in the echo of the second signal. Advantageously, this determination of the pressure in the anatomic vessel is non-invasive, as it is based on force applied to skin of the vertebrate and an echo received by the piezoelectric crystal. Further, or instead, because the second signal is sent by the piezoelectric crystal and is received by the same piezoelectric crystal, this determination of pressure in the anatomic vessel may be implemented using simplified hardware, as compared to the use of ultrasound transducer arrays arranged for two-dimensional and/or three-dimensional arrays. In general, determining the pressure in the anatomic vessel may include locating the anatomic vessel such that the first signal and the echo of the second signal correspond to the anatomic vessel of interest. In some implementations, locating the anatomic vessel may include the use of subjective techniques, such as visual inspection, which may be appropriate for anatomic vessels generally located near the skin surface. Additionally, or alternatively, determining the pressure in the anatomic vessel may include detecting presence of the anatomic vessel based on the one or more peaks of in the echo of the second signal. That is, force may be applied along the skin surface above the general vicinity of the anatomic vessel to be measured. The resulting force response, detectable as changes in one or more peaks in the echo of the second signal, may form a basis for determining the location of the anatomic vessel below the skin surface of the vertebrate. As a specific example, described in greater detail below with respect to experimental results obtained using a prototype system, the location of the IJV in proximity to the carotid artery in the neck of the vertebrate may correspond to a distinct distribution of peaks in the echo of the second signal as force is applied to the skin surface along the neck of the vertebrate. Detecting this unique distribution of the one or more peaks in the echo of the second signal may form a basis for locating the IJV below the surface of the skin of the vertebrate.

As force is applied to skin of the vertebrate above the location of the anatomic vessel, the first signal may be indicative of the magnitude of a component of the force exerted on the anatomic vessel. As the force applied to skin of the vertebrate is increased, the walls of the anatomic vessel may move closer to one another until the previously separated walls contact one another. This condition, referred to herein as collapse, may be detected based on the echo of the second signal. For example, detecting collapse of the anatomic vessel may include identifying merger of two discrete peaks into a single peak (e.g., as shown in the schematic representations of idealized echo in FIGS. 3A and 3B). The force corresponding to the time at which the merger of the discrete peaks of the echo may be recorded. Further, or instead, this force may be converted to pressure in the anatomic vessel, based on a known contact area over which the force is applied to skin of the vertebrate and Laplace's Law, as described above.

The anatomic pressure of the anatomic vessel is a quantitative assessment and, as such, determining the anatomic pressure may include calibrating one or both of the first signal and the echo of the second signal. In this context, calibration should be understood to include any manner and form of predetermined modification of the first signal or the echo of the second signal, as the case may be, to improve correlation between determined anatomic pressure and a known standard of the anatomic pressure. The known standard of the anatomic pressure may be, for example, an invasive measurement of the anatomic pressure of one or more model subjects.

As an example of calibration, the first signal may be calibrated based on a body mass index of the vertebrate. For example, calibration according to body mass index may be useful for accounting for differences in force transmission through muscle and fat. As used in this context, the body mass index may be any function of mass to one or more dimensions of the vertebrate. In instances in which the vertebrate is a human, the body mass index may be a quantity derived as a function of mass and height of the human.

As an additional or alternative example of calibration, the first signal may be calibrated based on depth of the anatomic vessel from the skin surface of the vertebrate in the absence of force applied to the skin. The depth of the anatomic vessel may be based on the echo of the second signal. For example, the depth of the anatomic vessel may be determined by one of the peaks in the echo of the second signal.

As still a further or alternative example of calibration, the first signal may be calibrated based on a width of the anatomic vessel in a direction parallel to the axis and in the absence of the force applied to the skin of the vertebrate. This width may be determined, for example, based on the echo of the second signal. More specifically, the width of the anatomic vessel or a parameter scaling with the width of the anatomic vessel may be determined based on a difference between discrete peaks in the echo of the second signal, with the discrete peaks corresponding to walls of the anatomic vessel as described herein. In certain implementations, the width used as a calibration parameter may be the shortest width of the anatomic vessel determined through repeated applications of force at different angles to the surface of the skin, as described in greater detail below.

The number and type of calibration parameters may be a combination of any of various different calibration parameters useful for achieving measurement accuracy required or useful for a particular application. Thus, it should be appreciated that other calibration parameters may additionally or alternatively be useful for improving the absolute measurement accuracy of the determined pressure of the anatomic vessel. Examples of additional or alternative calibration parameters may include: type of vertebrate; age of the vertebrate: sex of the vertebrate, the type of anatomic vessel being measured, with different calibration parameters for veins and arteries; medical history factors; and combinations thereof.

While calibration has been described as being useful for improving accuracy of the measured pressure, accuracy may further or instead be influenced by any of various different measurement artifacts associated with acquiring the signals forming basis of the pressure determination. For example, certain measurement artifacts may arise from the challenge in ascertaining relative position of the axis relative to the anatomic vessel. As an additional or alternative example, some measurement artifacts may be associated with the physical process of applying force along the axis to determine the pressure in the anatomic vessel. Thus, in certain implementations, determining the pressure in the anatomic vessel may include one or more techniques useful for at least partially removing the influence of measurement artifacts. Through execution of these techniques, the accuracy of the determination of pressure may be less prone the skill of the physician and, thus, more widely deployable across a wide variety of clinical settings.

In certain implementations, determining the pressure in the anatomic vessel may include at least partially removing measurement artifacts associated with tissue above the anatomic vessel being measured. For example, at least a portion of the force exerted on the skin surface may be absorbed by the tissue above the anatomic vessel being measured before the force exerted on the skin begins compressing the anatomic vessel. Stated differently, below a threshold, the force exerted on the skin surface of the vertebrate does not compress the anatomic vessel because this force is absorbed by the tissue above the anatomic vessel. To account for the force absorbed by the tissue, the pressure in the anatomic vessel may be determined based on a difference between the first signal at a first time and the received first signal at a second time different from the first time. The received first signal at the first time may correspond to initial movement of discrete peaks in the echo of the second signal in response to the force applied to the skin, and the received first signal at the second time may correspond to merger of the previously discrete peaks in the echo of the second signal in response to the force applied to the skin. Thus, the difference between the first signal at the first time and the second time represents only the force compressing the anatomic vessel and advantageously removes the portion of the force compressing the tissue.

In some instances, measurement artifacts may be attributable to small changes in position of the applied force relative to the anatomic vessel as the force is applied to the skin surface of the vertebrate in a nominally fixed orientation. These small changes in position may arise, for example, from small movements of the physician's hand as the force is applied to the skin surface of the vertebrate. To reduce the potential influence of such small changes on the measured pressure, determining the pressure in the anatomic vessel may be based on the first signal and the one or more peaks of the echo of the second signal over multiple applications of force to the skin of the vertebrate. For example, determining the pressure in the anatomic vessel may include averaging the determined pressures over the multiple applications of force. Additionally, or alternatively, determining the pressure in the anatomic vessel may include removing high and low determined pressures over the multiple applications of force. More generally, determining the pressure in the anatomic vessel may include any manner and form of processing information directly or indirectly related to the first signal and the echo of the second signal over the multiple applications of force to the skin of the vertebrate.

In certain instances, measurement artifacts may be attributable to physical attributes of hardware used to measure the first signal and/or the echo of the second signal. For example, the piezoelectric crystal may produce a beam having a nearfield in which constructive and destructive wave interference produce fluctuations that may interfere with signal processing of the echo of the second signal to identify the one or more peaks of the echo of the second signal. Thus, in some instances, determining pressure in the anatomic vessel may include canceling the nearfield of the echo of the second signal. In general, the nearfield is a function of the diameter of the piezoelectric crystal, the frequency at which piezoelectric crystal is driven, and the speed of sound in the tissue. Accordingly, the nearfield may vary according to the implementation of the piezoelectric crystal. In some useful implementations, however, the nearfield may be less than about the first 100 microseconds (e.g., less than about 10 microseconds) of the echo of the second signal in the time domain.

In general, signal processing of the first signal and/or the echo of the second signal may be additionally or alternatively useful for improving accuracy of determining pressure in the vessel. As used in this context, signal processing shall be understood to include any one or more of various different filters applied to raw data acquired from the force sensor and/or the from the piezoelectric crystal, as the case may be, and generally useful for facilitating any one or more of the techniques described herein. Thus, by way of example, signal processing may include applying one or more filters to the echo of the second signal to facilitate programmatically making determinations about the one or more peaks of the echo. As a more specific example, receiving the echo of the second signal may include applying a Hilbert transform to the echo of the second signal in a time domain. Thus, continuing with this example, determining the pressure in the anatomic vessel may include detecting the one or more peaks in the echo based on the Hilbert-transformed signal.

FIG. 5 is a flow chart of an exemplary method 500 of using a diagnostic system to non-invasively assess of an anatomic vessel of a vertebrate. Unless otherwise specified or made clear from the context, the exemplary method 500 may be carried out by a physician using any one or more of the devices and systems described herein. Thus, for example, the exemplary method 500 may be performed by a physician using the diagnostic system 100 (FIG. 1) to assess an anatomic vessel of a vertebrate.

As shown in step 502, the exemplary method 500 may include detecting an anatomic vessel below skin of the vertebrate. In certain implementations, such as those in which the anatomic vessel of interest is superficial, the anatomic vessel may be detected by visual inspection, palpitation, or a combination thereof. Additionally, or alternatively, to facilitate more objective and/or accurate location of the anatomic vessel below skin of the vertebrate, the anatomic vessel may be detected based on a force response of the anatomic vessel, as determined according to any one or more of the techniques described herein.

In general, the anatomic vessel may be any one or more of the anatomic vessels of the vertebrate and, thus, may be a vein or an artery. For example, the anatomic vessel may be the IJV of the vertebrate, from which the JVP may be non-invasively measured. Because JVP and IVV status are closely correlated, the non-invasive measurement of the JVP may advantageously provide a non-invasive assessment of IVV status. In turn, continuing with this example, the non-invasive assessment of IVV status may provide a useful basis for one or more clinical decisions that are typically based on invasive measurements.

As shown in step 504, the exemplary method 500 may include applying a force to skin of the vertebrate along an axis extending through a piezoelectric crystal and the anatomic vessel below the skin. That is, the force may be applied in a direction based on the location of the anatomic vessel below the skin. Additionally, or alternatively, this force may be applied by a physician manipulating a diagnostic system (e.g., the diagnostic system 100) according to any one or more of the techniques described herein to transmit force from a skin surface to an anatomic vessel below the skin surface. In the force may be applied for a period sufficient to obtain appropriate signals indicative of the force response of the anatomic vessel. The period may be, for example, greater than about 2 seconds and less than about 30 seconds, although shorter or longer periods are possible.

Returning to the example of assessment of the IJV, applying the force to skin of the vertebrate may include placing the piezoelectric crystal along a base of a neck of the vertebrate. More specifically, in instances in which the vertebrate is a human, placing the piezoelectric crystal along the base of the neck of the vertebrate may include placing the piezoelectric crystal such that the axis of application of the force passes through a triangle defined by a clavicle and two heads of a sternocleidomastoid of the vertebrate. This orientation may be particularly useful for measurement of the IJV as it is where the IJV is most superficial and anatomically separated from the external jugular vein. That is, in other orientations, other anatomic structures, such as the external jugular vein, may interfere with characteristics of an echo used to assess the IJV.

As shown in step 506, the exemplary method 500 may include receiving a first signal from a force sensor. As shown in step 508, the exemplary method 500 may include sending a second signal from the piezoelectric crystal toward the anatomic vessel in a direction substantially parallel to the axis. As shown in step 510, the exemplary method 500 may include receiving an echo of the signal at the piezoelectric crystal. As shown in step 512, the exemplary method 500 may include determining pressure in the anatomic vessel based on the first signal and one or more peaks in the echo. Unless otherwise specified or made clear from the context, steps 506, 508, 510, and 512 shall be understood to be analogous to steps 402, 404, 408, and 408, respectively, of the exemplary method 400 (FIG. 4). Accordingly, for the sake of efficient description, these steps are not discussed separately.

While the exemplary method 500 has been described in the context of a single axis, it should be appreciated that the exemplary method 500 may include identification of the single axis in certain implementations. This may be particularly useful in instances in which a relative orientation of the skin surface to the anatomic vessel is unknown. In general, it may be desirable to orient the axis substantially perpendicular to an axial dimension of the anatomic vessel such that the force is applied to the anatomic vessel in a radial direction. However, without knowledge of relative orientation between the skin surface and the anatomic vessel, it may be advantageous to orient the axis based on the one or more peaks in the echo of the second signal. Thus, in some instances, applying the force to the skin of the vertebrate may further or instead include moving the axis relative to the anatomic vessel through a plurality of angles and, at each angle, determining a respective width of the anatomic vessel based on the one or more peaks in the echo of the signal. These widths may be useful for identifying a direction substantially perpendicular to an axial dimension of the anatomic vessel. That is, the smallest width corresponds to the substantially perpendicular direction, as each of the other widths correspond to directions having an axial directional component along the axis of the anatomic vessel. Continuing with this example, the force may be applied in a direction substantially parallel to a smallest width in a plurality of widths corresponding to the plurality of angles.

Experiments

The following experiments describe one or more aspects of assessing an IJV of a vertebrate in accordance with one or more of the exemplary methods described herein. It is to be understood, however, that these experiments and corresponding results are set forth by way of example only, and nothing in these examples shall be construed as a limitation on the overall scope of the disclosure. Thus, for example, while these experiments are described with respect to the IJV of vertebrates, this should not be understood to limit the techniques described herein.

All experiments were performed with multiple samples from independent conditions. The data are represented as the mean of the independent replicates. To the extent shown, error bars represent the standard deviation of the sample. All analysis was performed using the Statistics Toolbox in MATLAB (available from MathWorks® of Natick, Mass.).

Experimental Set-Up

In each of the following experiments, an experimental diagnostic system was used. Unless otherwise specified or made clear from the context, this experimental diagnostic system is based on the operating principles of the diagnostic system 100 (FIG. 1) described above. However, for the sake of ease of experimentation, the experimental diagnostic system was a lab bench implementation of principles of the diagnostic system 100. Accordingly, certain aspects of the experimental diagnostic system were implemented using off-the-shelf components and software, and additional components were included for the sake of data acquisition.

In particular, a 1 MHz single crystal ultrasound probe (available from Olympus America, Inc. of Center Valley, Pa.) was utilized to transmit an ultrasound pulse generated by a JSR Ultrasonics DPR300 Pulser (available from Imaginant Inc., Pittsford, N.Y.) and to receive the echo (a raw A mode pulse echo scan) of the ultrasound pulse. The central frequency of 1 MHz in the crystal unit ensured the optimum resolution (order of 1 mm) and minimize attenuation in the ultrasound signals to locate the IJV or model representation of the IJV, as the case may be in the experiments described below. Higher frequency ultrasound suffers from more attenuation and low frequency ultrasound suffers from poor resolution. The echo was converted from an analog to a digital signal by an ultrasound DAQ system, such as a PicoScope 5000 Series available from Pico® Technology of Cambridgeshire, United Kingdom, at a sampling rate of 2 GS/s to minimize quantization noise.

The normal force to transiently collapse the IJV or the model representation of the IJV in the experiments below was measured by a FUTEK LRF400 load cell (having model number FSH000262 and available from FUTEK Advanced Sensor Technology, Inc., of Irvine, Calif.), which outputs a low analog voltage signal with a maximum range of ±2 mV. This voltage was amplified to a range of ±10 V by a FUTEK IAA100 Differential Amplifier (available from FUTEK Advanced Sensor Technology, Inc., of Irvine, Calif.). The amplified voltage signal was converted to a digital signal by an NI DAQ USB 6001 (available from National Instruments of Austin, Tex.).

The single crystal ultrasound probe and the load cell were disposed in a housing in an orientation analogous to the arrangement of corresponding parts of the diagnostic system 100 (shown in FIGS. 2A and 2B). The housing was formed of acrylonitrile butadiene styrene (ABS) plastic (ABSplus) and was shaped to hold the single crystal ultrasound probe axially aligned with the load cell. The single crystal ultrasound probe and the load cell in the housing were in electrical communication with other components outside of the housing via wires extending from the housing to the other components as necessary.

The digitized force signal and the echo signal were processed in LabView (available from National Instruments of Austin, Tex.) to calculate pressure in the IJV. More specifically, the baseline force immediately when the IJV started collapsing was subtracted from the force at which the IJV was focally collapsed, with this subtraction being useful for removing forces that contribute to compressing tissue above the IJV. LabView converted the resulting force to a pressure measurement according to the relationship: $P=F/A$, where P is pressure, F is the force, and A is the contact area of the single crystal ultrasound probe on the skin of the subject. This pressure was normalized by the subject's body mass index (BMI) to account for the lower percentage of applied pressure contributing to IJV collapse given a higher BMI. This normalized pressure was the JVP corresponding to the IJV.

For each experiment below performed on a human subject, the housing was positioned along the base of the right side of the neck of bordered by the sternal and clavicular head of the sternocleidomastoid muscle medially and laterally, and the clavicle ventrally, in a position analogous to the position of the diagnostic system 100 shown in FIG. 1. The application of force to the housing, in turn, may cause compression and collapse of the IJV.

Experimental Analysis of Model System of the IJV

Model systems of the UV were made with gelatin, interspersed with cornstarch to provide measuring landmarks. The model system included three balloons filled with different amounts of water to mimic various UV cross-sectional areas.

Figure 6C:
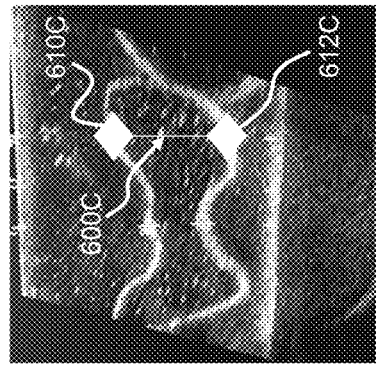
FIG. 6C is a cross-sectional sonogram image of the anatomic analog of FIG. 4A, with the balloon of the anatomic analog in an empty state.
Figure 6B:
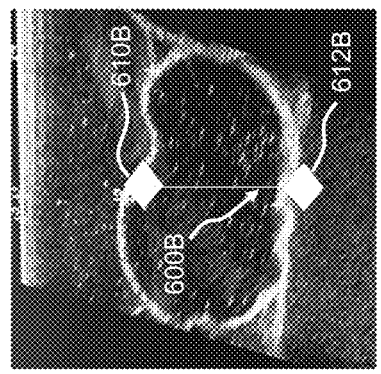
FIG. 6B is a cross-sectional sonogram image of the anatomic analog of FIG. 4A, with the balloon of the anatomic analog in a partially filled state.
Figure 6A:
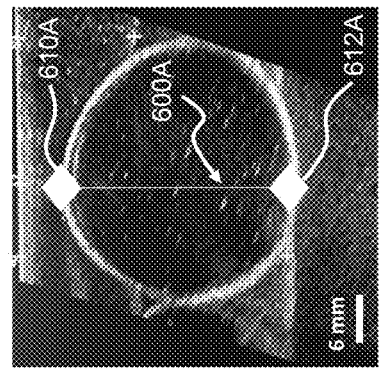
FIG. 6A is a cross-sectional sonogram image of an anatomic analog including a balloon within gelatin molds, with the balloon in a fully filled state.

Referring now to FIGS. 6A-6C, the cross-sectional diameters of the balloons were measured in triplicate with two-dimensional ultrasound using a GE Ultrasound Logiz E9 (available from GE Healthcare of Chicago, Ill.) as a control. Such two-dimensional ultrasound may be referred to below as conventional two-dimensional ultrasound.

Figures 7A, 7B, 7C:
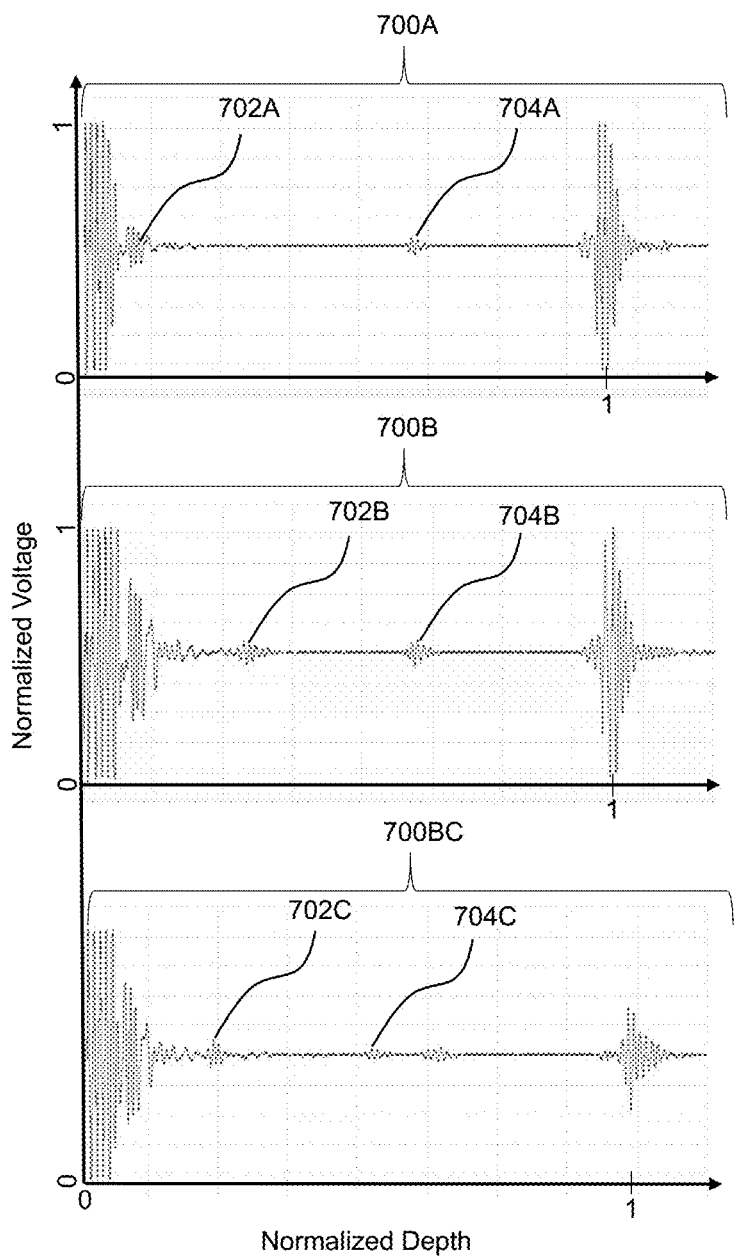
FIG. 7A is a single-crystal ultrasound acoustic profile of the anatomic analog in the fully filled state corresponding to FIG. 4A, the profile measured using the diagnostic system of FIG. 1.
FIG. 7B is a single-crystal ultrasound acoustic profile of the anatomic analog in the partially filled state corresponding to FIG. 4B, the profile measured using the diagnostic system of FIG. 1.
FIG. 7C is a single-crystal ultrasound acoustic profile of the anatomic analog in the empty state corresponding to FIG. 4C, the profile measured using the diagnostic system of FIG. 1.

Referring now to FIGS. 7A-7C, the experimental setup was used to measure the thickness of gelatin above the balloons, the lumen of the balloons, and the thickness of gelatin between the bottom of the balloon and the cornstarch layer. FIG. 7A is a graphical representation of a single crystal acoustic profile 700A along a line 600A in the corresponding 2-D ultrasound image in FIG. 6A. Similarly, FIG. 7B is a graphical representation of a single crystal acoustic profile 700B corresponding to a line 600B in the corresponding 2-D ultrasound image in FIG. 6B. Likewise, FIG. 7C is a graphical representation of a single crystal acoustic profile 700C corresponding to a line 600C in the corresponding 2-D ultrasound image in FIG. 6C. The single crystal acoustic profiles 700A-C are feature scale normalized such that each acoustic profile is represented as normalized voltage as a function of normalized depth. In general, the single crystal acoustic profiles 700A-C should be understood to be measured profiles similar to the idealized profile of the echo 300 in FIGS. 3A and 3B.

Referring now to FIGS. 6A-7C, it should be appreciated that the walls of the balloons shown in FIGS. 6A-6C are observable as echo peaks in the respective single crystal acoustic profile in FIGS. 7A-7C. That is, comparing FIG. 6A to FIG. 7A, it may be observed that walls 610A and 612A in FIG. 6A are represented as discrete peaks 702A and 704A in the single crystal acoustic profile 700A in FIG. 7A. Similarly, comparing FIG. 6B to FIG. 7B, it may be observed that walls 610B and 612B in FIG. 6B are represented as discrete peaks 702B and 704B in the single crystal acoustic profile 700B in FIG. 7B. Likewise comparing FIG. 6C to FIG. 7C, it may be observed that walls 610C and 612C in FIG. 6C are represented as discrete peaks 702C and 704C. Further, the distance between the respective discrete peaks in each FIGS. 7A to 7C correspond to a change in the relative distance of the walls in FIGS. 6A to 6C, suggesting that the discrete echo peaks measured by the single crystal ultrasound probe may be useful for providing quantitative information regarding the size of anatomic vessels of test subjects.

Experimental Measurement of IJV Diameter

Figure 8:
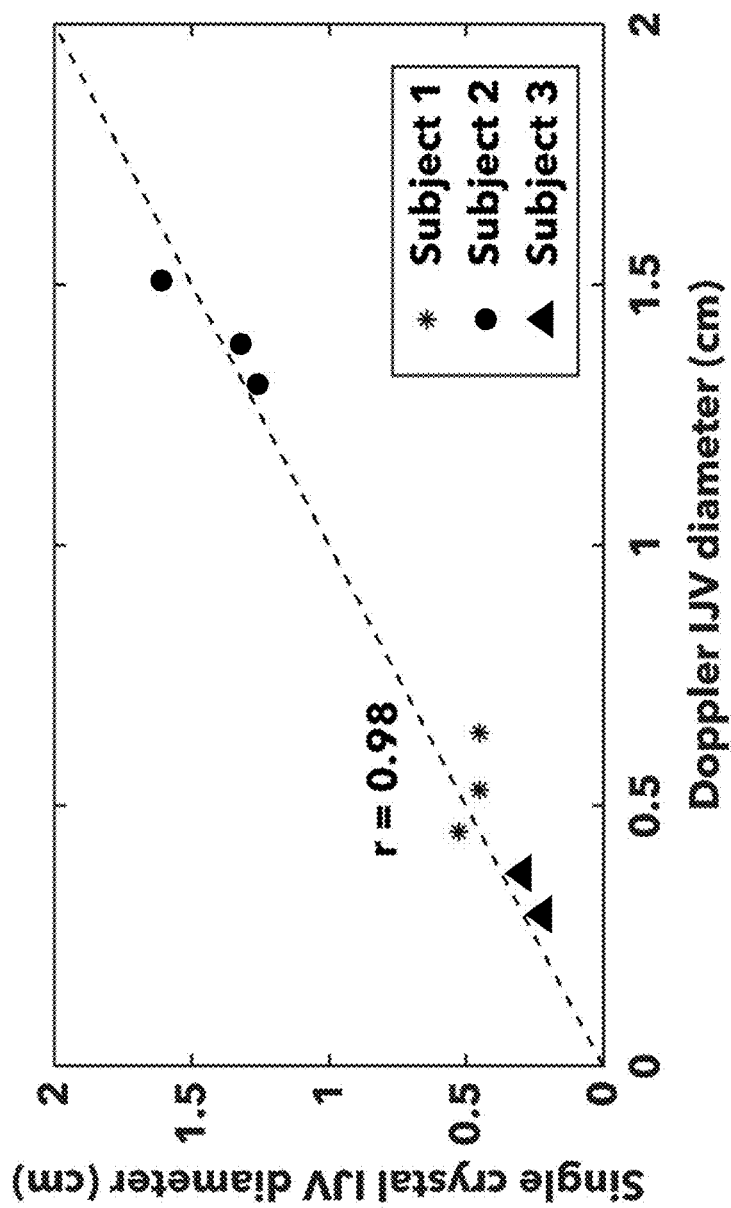
FIG. 8 is a graphical comparison of sonographic measurement and single crystal ultrasound measurement of diameters of internal jugular veins of three human subjects in a standing position.

Referring now to FIG. 8, IJV diameters of three test subjects were measured using conventional imaging ultrasound and using the single crystal ultrasound probe. In particular, the IJV diameters measured using the single crystal ultrasound probe were based on distance between discrete peaks in the echo. As indicated above, these discrete echo peaks are indicative of the position of the walls of the vessel and, thus, useful for determining diameter of the IJV. As shown in FIG. 8, the vessel diameters determined through assessment of the discrete peaks in the echo acquired with single crystal ultrasound probe were in close agreement with the vessel diameters measured using conventional two-dimensional ultrasound (Pearson's correlation coefficient, $r=0.98$). Further, the measurements for each subject were observed to be tightly clustered, which suggests high measurement repeatability with the single crystal ultrasound probe. Accordingly, based at least in part on these results, the echo measured by the single crystal ultrasound probe may be useful for locating and detecting walls of the IJV.

Experimental Detection of IJV Location

Figure 9B:
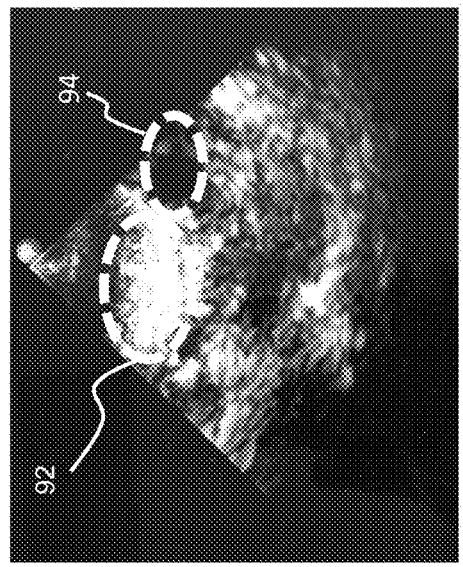
FIG. 9B is a sonogram image of the anatomic region of FIG. 9A, with the internal jugular vein in a collapsed state.
Figure 9A:
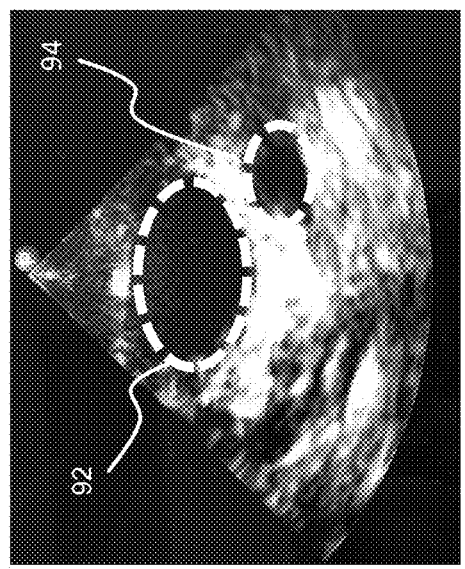
FIG. 9A is a sonogram image of an anatomic region including an internal jugular vein of a vertebrate, with the internal jugular vein in a basal state.
Figures 10A, 10B:
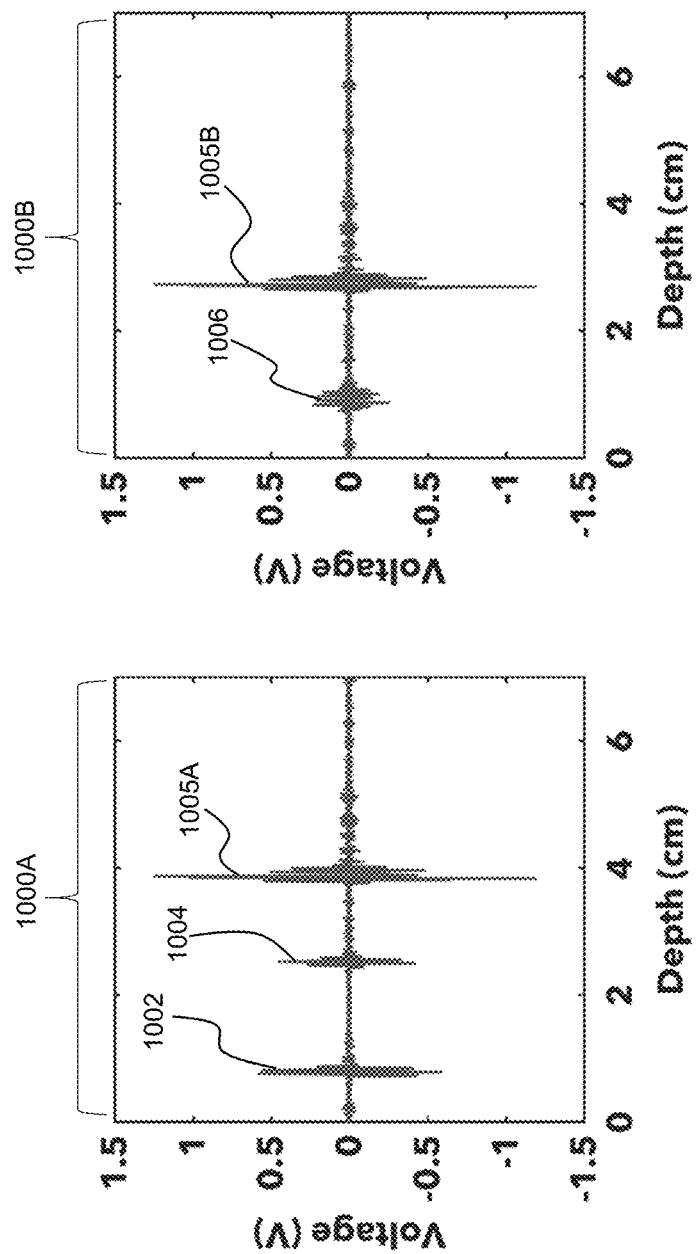
FIG. 10A is a single-crystal ultrasound acoustic profile of the anatomic region in the state shown in FIG. 9A, the profile measured using the diagnostic system of FIG. 1.
FIG. 10B is a single-crystal ultrasound acoustic profile of the anatomic region in the state shown in FIG. 9B, the profile measured using the diagnostic system of FIG. 1.

Referring now to FIGS. 9A-10B, the IJV of a test subject was located using the single crystal ultrasound probe. In particular, using conventional imaging ultrasound imaging, the location of an IJV 92 was identified by its steady state flow profile and position above a carotid artery 94, as shown in the sonogram image in FIG. 9A. Identification of the IJV 92 was confirmed by applying pressure to the conventional imaging ultrasound probe to collapse the IJV 92, noting the carotid artery 94 remained open, as shown in the sonogram image in FIG. 9B. As shown in FIG. 10A, with the housing placed at the same location as the conventional imaging ultrasound probe, a corresponding echo 1000A measured using the single crystal ultrasound probe revealed two discrete peaks 1002 and 1004 indicative of the walls of the IJV 92 in the basal state (FIG. 9A) and a larger peak 1005A indicative of the near-side wall of the carotid artery 94 (FIG. 9A). As shown in FIG. 10B, as force is applied to the housing and, in turn, to the neck of the test subject, a corresponding one of the echoes 1000B measured using the single crystal ultrasound probe revealed a collapsed peak 1006 indicative of the walls of the IJV 92 in the focally collapsed state (FIG. 9B) and a larger peak 1005B indicative of the near-side of the carotid artery 94 (FIG. 9B).

In use, the location of the IJV 92 may be determined by applying force to the neck of the vertebrate at different locations. The location of the IJV 92 may be determined to correspond to the location in which the applied force results in the two discrete peaks 1002 and 1004 collapsing to a single peak 1006 as the near-side of the carotid artery 94 remains observable as a large peak 1005. While this location technique has been described in terms of graphical representations of the echoes 1000A and 1000B as force is applied, it should be appreciated that this technique may further or instead be carried out through signal processing of the echoes 1000A and 1000B, without a graphical or other display of the echoes 1000A and 1000B.

Experimental Measurement of JVP

Figure 11:
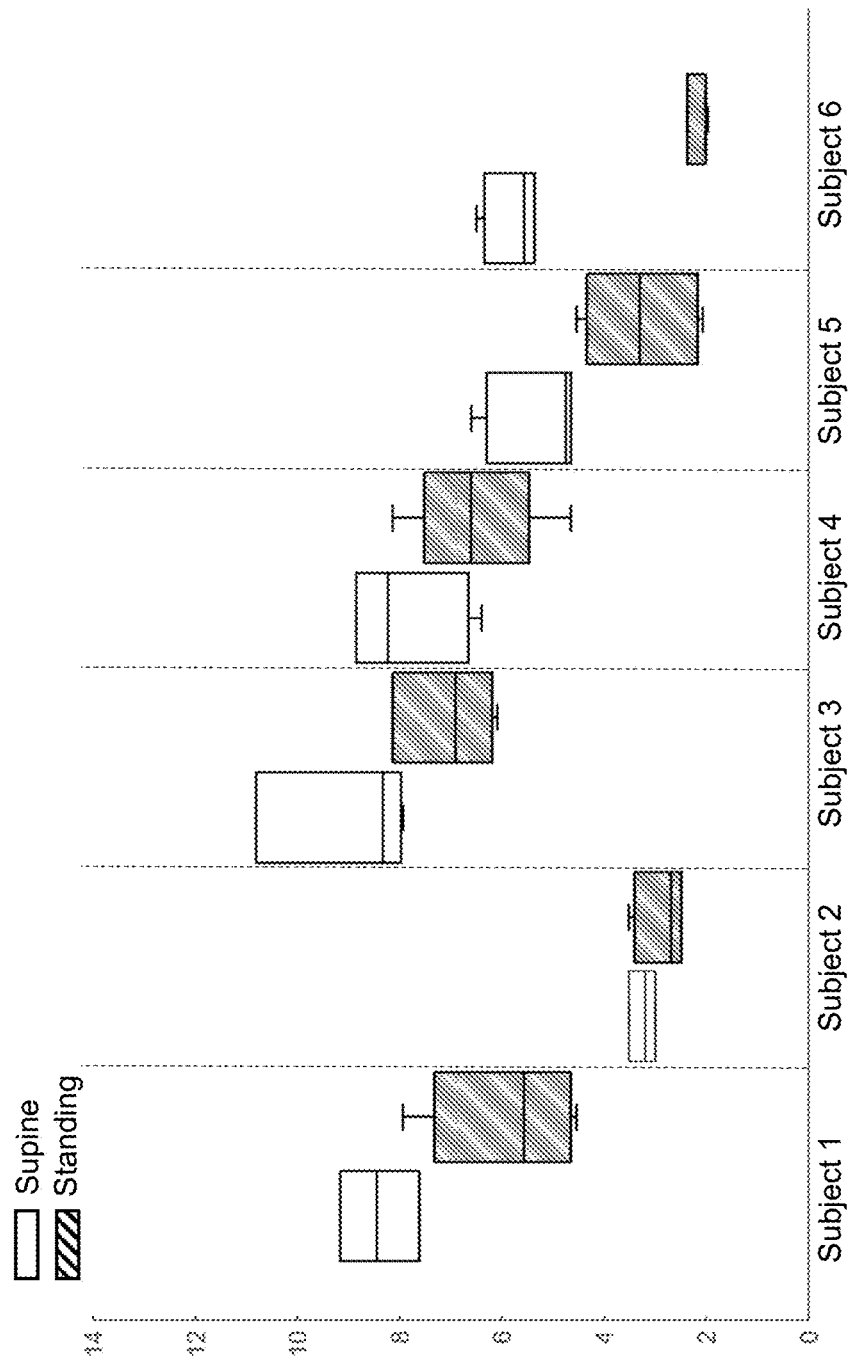
FIG. 11 is a graphical representation of relative changes in jugular venous pressure of six human subjects in supine and standing positions.

Referring now to FIG. 11, the JVP of six healthy human volunteers (1 female and 5 males, between the ages of 22 and 40) was measured with each volunteer in supine and standing positions. The JVP was measured by applying force from the housing to the neck of the vertebrate to collapse the IJV. The collapse was determined based on the collapse of distinct echo peaks to a single peak as described herein, and the force corresponding to the collapse was recorded. In turn, the force corresponding to the collapse of the IJV was converted to the JVP, as also described herein. A student's two-tailed t-test was performed to determine significant differences between standing and supine JVP measurements ($p<0.05$).

In general, the position of the IJV relative to the heart is expected to result in altered volumetric venous blood flow. For example, in a supine position, the IJV of a given subject is level with the right atrium of the heart and, thus, experiences increased blood volume. The increased blood volume associated with the supine position, in turn, is expected to correspond to an increase in the JVP for the respective subject. This pattern is observed in FIG. 11, which shows that there was a statistically significant difference in JVP between standing and supine postures among the subjects ($p<0.0001$).

While certain implementations have been described, other implementations are additionally or alternatively possible.

For example, while diagnostic systems have been described as being useful for determining the location of anatomic vessels, determining the size of such vessels, determining pressure in such vessels, and combinations thereof, it should be appreciated that the diagnostic system may additionally or alternatively be used for other types of assessments of anatomic vessels. In some instances, for example, the diagnostic system may determine tissue health of one or more walls of the anatomic vessel. As a more specific example, the determination of health of the one or more walls of the anatomic vessel may be based on an area under one or more peaks of a Hilbert-transformed echo of the second signal. Such a determination of tissue health may be useful for diagnosing additional conditions and, in general, assessing vascular health of a vertebrate.

As another example, while a single piezoelectric crystal has been described as being used to send an acoustic signal and receive an echo of the acoustic signal, other configurations for sending an acoustic signal and receiving an echo may be useful. For example, referring now to FIG. 12, a diagnostic system 100' may include a force sensor 1202, first piezoelectric crystal 1204A, a second piezoelectric crystal 1204B, and a controller 1206. Unless otherwise specified or made clear from the context, elements designated by 1200-series numbers should be understood to be analogous to corresponding elements designated by 200-series numbers in FIGS. 2A and 2B. Thus, for the sake of efficient description, 1200-series elements are not discussed separately, except to point out differences from the corresponding elements designated by 200-series numbers in FIGS. 2A and 2B. For example, the controller 1206 may be in electrical communication with one or more of the force sensor 1202, the first piezoelectric crystal 1204A, and the second piezoelectric crystal 1204B. Further, or instead, the first piezoelectric crystal 1204A and the second piezoelectric crystal 1204B may each be substantially identical to the piezoelectric crystal 204 (FIG. 2).

In use, the diagnostic system 100' may be operated in a manner generally similar to the diagnostic system 100 (FIG. 1) discussed above. The first piezoelectric crystal 1204A may direct an acoustic pulse toward an anatomic vessel along an axis 1214, and the second piezoelectric crystal 1204B may receive an echo from the acoustic pulse. That is, more generally, the acoustic pulse and the echo are sent and received from different piezoelectric crystals, and these piezoelectric crystals may be positioned closed to one another (e.g., with a small angle between the piezoelectric crystals such that the acoustic pulse and the echo are substantially parallel to one another). Further, or instead, the signals may be sent and received using only a few piezoelectric crystals (e.g., 2 or 3 piezoelectric crystals), which may advantageously provide size and complexity advantages relative to ultrasound transducer arrays.

Figure 12:
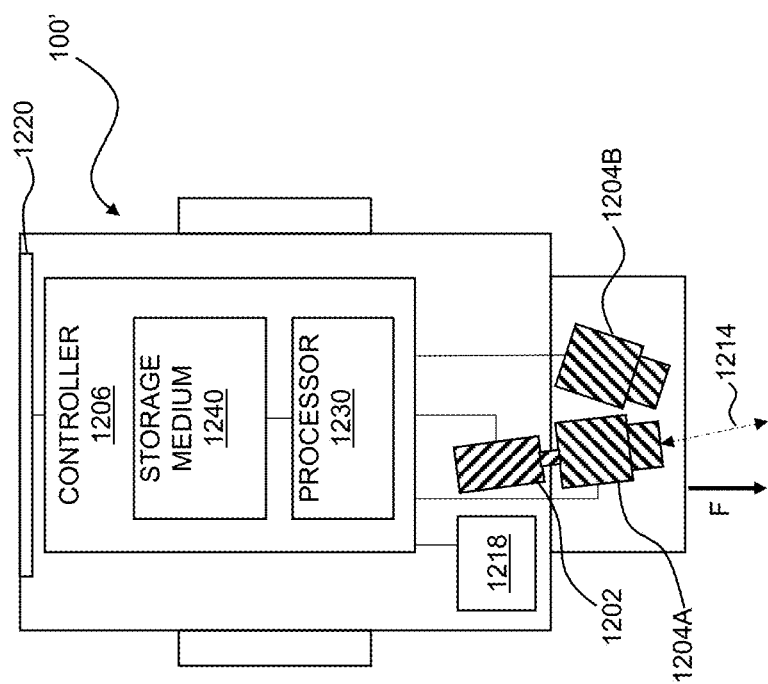
FIG. 12 is a schematic representation of a diagnostic system including a first piezoelectric crystal and a second piezoelectric crystal.
Figure 13:
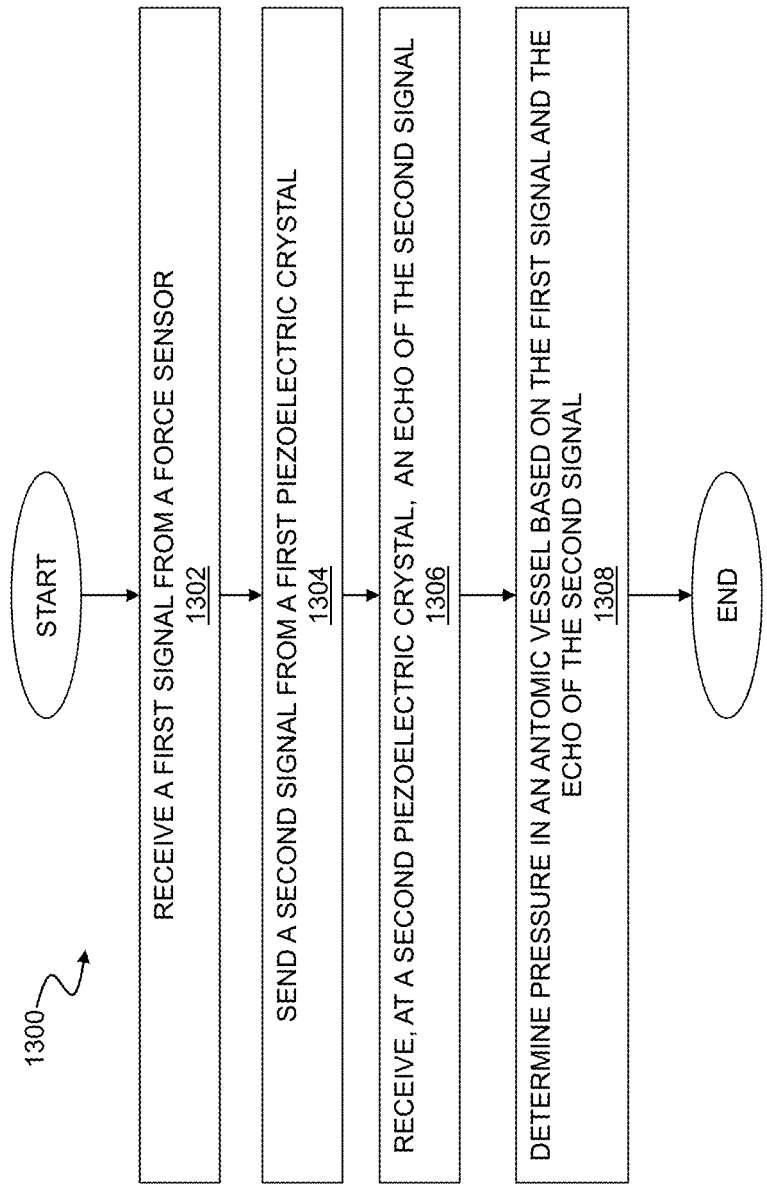
FIG. 13 is a flow chart of an exemplary method of non-invasive assessment of an anatomic vessel of a vertebrate using a diagnostic system including a first piezoelectric crystal and a second piezoelectric crystal.

FIG. 13 is a flow chart of an exemplary method 1300 of non-invasive assessment of an anatomic vessel of a vertebrate using a diagnostic system including a first piezoelectric crystal and a second piezoelectric crystal. In general, the exemplary method may be carried out using the diagnostic system 100' (FIG. 12).

As shown in step 1302, the exemplary method 1300 may include receiving a first signal from a force sensor. Unless otherwise specified or made clear from the context, the step 1302 shall be understood to be analogous to the step 402 in FIG. 4. Thus, for example, the first signal may be indicative of a force applied to skin of the vertebrate and transmitted along an axis extending through an anatomic vessel below the skin.

As shown in step 1304, the exemplary method 1300 may include sending a second signal from a piezoelectric crystal toward the anatomic vessel in a direction substantially parallel to the axis. In general, it should be understood that step 1304 is analogous to step 404 in FIG. 4, unless otherwise specified or made clear from the context. Thus, the second signal may be an ultrasound pulse.

As shown in step 1306, the exemplary method 1300 may include receiving an echo of the second signal at a second piezoelectric crystal different from the first piezoelectric crystal. In certain implementations, the second piezoelectric crystal may be positioned near the first piezoelectric crystal such that the echo is substantially parallel to the second signal.

As shown in step 1308, the exemplary method 1300 may include determining pressure in the anatomic vessel based on the first signal and one or more peaks in the echo of the second signal. The step 1308 should be generally understood to be analogous to the step 408 in FIG. 4 and, more generally, may include determining pressure in the anatomic vessel according to any one or more of the techniques described herein.

As a further example, while the diagnostic system has been described as being held by a physician and pressed against a skin surface of a vertebrate, other approaches to positioning the diagnostic system against the skin surface of the vertebrate are additionally or alternatively possible. For example, the diagnostic system may be secured in place against the skin surface of the vertebrate using one or more straps or other similar securing approaches. Securing the diagnostic system against the skin surface of the vertebrate may facilitate, among other things, non-invasively monitoring pressure in the anatomic vessel over an extended period of time.

The above systems, devices, methods, processes, and the like may be realized in hardware, software, or any combination of these suitable for a particular application. The hardware may include a general-purpose computer and/or dedicated computing device. This includes realization in one or more microprocessors, microcontrollers, embedded microcontrollers, programmable digital signal processors or other programmable devices or processing circuitry, along with internal and/or external memory. This may also, or instead, include one or more application specific integrated circuits, programmable gate arrays, programmable array logic components, or any other device or devices that may be configured to process electronic signals. It will further be appreciated that a realization of the processes or devices described above may include computer-executable code created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software. In another aspect, the methods may be embodied in systems that perform the steps thereof, and may be distributed across devices in a number of ways. At the same time, processing may be distributed across devices such as the various systems described above, or all of the functionality may be integrated into a dedicated, standalone device or other hardware. In another aspect, means for performing the steps associated with the processes described above may include any of the hardware and/or software described above. All such permutations and combinations are intended to fall within the scope of the present disclosure.

Embodiments disclosed herein may include computer program products comprising computer-executable code or computer-usable code that, when executing on one or more computing devices, performs any and/or all of the steps thereof. The code may be stored in a non-transitory fashion in a computer memory, which may be a memory from which the program executes (such as random access memory associated with a processor), or a storage device such as a disk drive, flash memory or any other optical, electromagnetic, magnetic, infrared or other device or combination of devices. In another aspect, any of the systems and methods described above may be embodied in any suitable transmission or propagation medium carrying computer-executable code and/or any inputs or outputs from same.

The method steps of the implementations described herein are intended to include any suitable method of causing such method steps to be performed, consistent with the patentability of the following claims, unless a different meaning is expressly provided or otherwise clear from the context. So, for example, performing the step of X includes any suitable method for causing another party such as a remote user, a remote processing resource (e.g., a server or cloud computer) or a machine to perform the step of X. Similarly, performing steps X, Y and Z may include any method of directing or controlling any combination of such other individuals or resources to perform steps X, Y and Z to obtain the benefit of such steps. Thus, method steps of the implementations described herein are intended to include any suitable method of causing one or more other parties or entities to perform the steps, consistent with the patentability of the following claims, unless a different meaning is expressly provided or otherwise clear from the context. Such parties or entities need not be under the direction or control of any other party or entity, and need not be located within a particular jurisdiction.

It will be appreciated that the methods and systems described above are set forth by way of example and not of limitation. Absent an explicit indication to the contrary, the disclosed steps may be modified, supplemented, omitted, and/or re-ordered without departing from the scope of this disclosure. Numerous variations, additions, omissions, and other modifications will be apparent to one of ordinary skill in the art. In addition, the order or presentation of method steps in the description and drawings above is not intended to require this order of performing the recited steps unless a particular order is expressly required or otherwise clear from the context. Thus, while particular embodiments have been shown and described, it will be apparent to those skilled in the art that various changes and modifications in form and details may be made therein without departing from the spirit and scope of this disclosure and are intended to form a part of the invention as defined by the following claims, which are to be interpreted in the broadest sense allowable by law.

What is claimed is:

1. A system comprising:
   a force sensor;
   a piezoelectric crystal, the force sensor disposed relative to the piezoelectric crystal to measure a force exerted along an axis extending through the piezoelectric crystal; and a controller in electrical communication with the force sensor and the piezoelectric crystal, the controller configured to perform operations comprising:
   receiving a first signal from the force sensor, the first signal indicative of the force exerted along the axis extending through the piezoelectric crystal and transmitted to an anatomic vessel below skin of a vertebrate,
   sending a second signal from the piezoelectric crystal toward the anatomic vessel in a direction substantially parallel to the axis,
   receiving, from the piezoelectric crystal, an echo of the second signal substantially along the axis, and
   based on the first signal and one or more peaks in the echo of the second signal, determining pressure in the anatomic vessel, wherein determining the pressure in the anatomic vessel includes detecting collapse of the anatomic vessel in response to the force, wherein detecting the collapse of the anatomic vessel includes identifying a merger of discrete peaks of the one or more peaks in the echo of the second signal by determining a difference between the first signal at a first time and the first signal at a second time different from the first time, the first signal at the first time corresponding to initial movement of the discrete peaks in response to the force, and the first signal at the second time corresponding to the merger of the discrete peaks in response to the force.

2. The system of claim 1, wherein the force sensor and the piezoelectric crystal are axially aligned with one another along the axis.

3. The system of claim 1, wherein determining the pressure in the anatomic vessel includes detecting a presence of the anatomic vessel, below the skin of the vertebrate, based on the one or more peaks in the echo of the second signal.

4. The system of claim 3, wherein determining the pressure in the anatomic vessel further includes, based on detecting the presence of the anatomic vessel, sending an indication of the presence of the anatomic vessel below the skin.

5. The system of claim 1, wherein determining the pressure in the anatomic vessel includes receiving one or more calibration parameters and calibrating the first signal based on the one or more calibration parameters.

6. The system of claim 5, wherein the one or more calibration parameters include one or more of a body mass index of the vertebrate, a gender of the vertebrate, a height of the vertebrate, a weight of the vertebrate, and body surface area of the vertebrate.

7. The system of claim 5, wherein the one or more calibration parameters include a depth of the anatomic vessel from a skin surface of the vertebrate in an absence of the force.

8. The system of claim 5, wherein the one or more calibration parameters include a width of the anatomic vessel in a direction parallel to the axis and in an absence of the force.

9. The system of claim 1, wherein determining the pressure in the anatomic vessel is based on the detected collapse of the anatomic vessel.

10. The system of claim 1, wherein the piezoelectric crystal is disposed relative to the force sensor such that, as the force is transmitted through the force sensor to the anatomic vessel, the piezoelectric crystal is between the force sensor and the anatomic vessel.

11. The system of claim 1, further comprising a housing, wherein the force sensor and the piezoelectric crystal are at least partially disposed in the housing, and the housing is sized for single-handed manipulation by a user.

12. The system of claim 11, wherein the controller is at least partially disposed in the housing.

13. The system of claim 11, further comprising a battery at least partially disposed in the housing, the battery in electrical communication with the force sensor, the controller, and the piezoelectric crystal.

14. The system of claim 11, further comprising a user interface carried on the housing, wherein the user interface is in electrical communication with the controller, and the controller is further configured to send an indication of the pressure in the anatomic vessel to the user interface.

15. The system of claim 1, wherein the controller is further configured to determine pressure in the anatomic vessel based on a predetermined contact area of the force sensor.

16. The system of claim 15, wherein the axis extends through the predetermined contact area of the force sensor.

17. The system of claim 1, wherein determining the pressure in the anatomic vessel is based on the first signal and at least one peak of the echo of the second signal produced by multiple applications of the force.

* * * * *